United States Patent [19]

Clough et al.

[11] Patent Number: 5,124,329

[45] Date of Patent: Jun. 23, 1992

[54] FUNGICIDES

[75] Inventors: John M. Clough, Buckinghamshire; Ian T. Streeting; Christopher R. A. Godfrey, Bracknell, all of England

[73] Assignee: Imperial Chemical Industries PLC, London, England

[21] Appl. No.: 544,544

[22] Filed: Jun. 28, 1990

[30] Foreign Application Priority Data

Jun. 28, 1989 [GB] United Kingdom ............... 8914797
Nov. 13, 1989 [GB] United Kingdom ............... 8925612

[51] Int. Cl.$^5$ ................. C07D 251/46; C07D 251/30; C07D 251/16; A01N 43/66

[52] U.S. Cl. ..................... 514/241; 514/242; 514/245; 544/219; 544/211; 544/212; 544/218; 544/198; 544/207; 544/209; 544/182

[58] Field of Search .............. 544/182, 219, 211, 212, 544/218, 198, 207, 209; 514/245, 242

[56] References Cited

U.S. PATENT DOCUMENTS 4,931,438 6/1990 Clough et al. ..................... 544/213

OTHER PUBLICATIONS

Clough et al., Chemical Abstracts, vol. 109, entry 50255b (1988).

*Primary Examiner*—John M. Ford
*Attorney, Agent, or Firm*—Cushman, Darby & Cushman

[57] ABSTRACT

Fungicidal compounds having the formula (I):

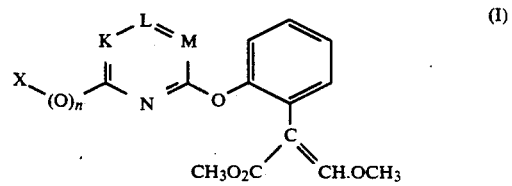

in which any two of K, L and M are nitrogen and the other is CY wherein Y is H, halogen, $C_{1-4}$ alkyl, $C_{1-4}$ alkoxy, cyano, nitro or trifluoromethyl; n is 0 or 1 and X is an optionally substituted aromatic or heteroaromatic ring.

6 Claims, No Drawings

FUNGICIDES

This invention relates to derivatives of propenoic acid useful as fungicides, to processes for preparing them, to fungicidal compositions containing them, and to methods of using them to combat fungi, especially fungal infections of plants.

There is described in EP-A-0260794 a range of fungicidal compounds which are methyl 2-(optionally substituted)heterocyclyloxy(or thio)phenyl-3-methoxypropenoates. The heterocyclic ring is six-membered, C-linked and contains 2 to 4 nitrogen atoms. Included are triazinyloxy compounds.

According to the present invention there are provided compounds having the formula (I):

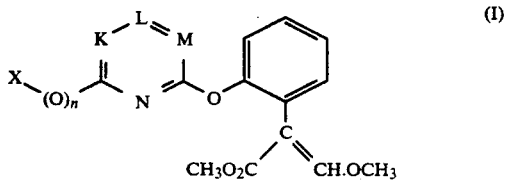

in which any two of K, L and M are nitrogen and the other is CY wherein Y is H, halogen, $C_{1-4}$ alkyl (for example, methyl), $C_{1-4}$ alkoxy (for example, methoxy), cyano, nitro or trifluoromethyl; n is 0 or 1; and X is an optionally substituted aromatic or heteroaromatic ring.

Because of the unsymmetrically substituted double bond of the propenoate group, the compounds of the invention may be obtained in the form of mixtures of (E) and (Z) geometric isomers. However, these mixtures can be separated into individual isomers, and this invention embraces such isomers and mixtures thereof in all proportions including those which consist substantially of the (Z)-isomer and those which consist substantially of the (E)-isomer. The (E)-isomer, in which the groups —$CO_2CH_3$ and —$OCH_3$ are on opposite sides of the olefinic bond of the propenoate group, are the more fungicidally active and form a preferred embodiment of the invention.

The ring

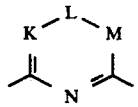

in formula (I) is a triazine ring. It may be a symmetrical triazine ring in which K and M are both nitrogen and L is CY or an unsymmetrical triazine ring in which either K and L are both nitrogen and M is CY or L and M are both nitrogen and K is CY.

The group Y is typically H or halogen, suitably chlorine.

The group X may be any optionally substituted aromatic or heteroaromatic ring. When it is an optionally substituted aromatic ring the aromatic ring is suitably phenyl. When it is an optionally substituted heteroaromatic ring the heteroaromatic ring may be, for example, one of the following rings, in each case linked from any atom of the ring X which valency allows: furan, thiophene, pyrrole, imidazole, pyrazole, thiazole, isothiazole, oxazole, isoxazole, 1,2,4-triazole, 1,2,3-triazole, 1,2,4-thiadiazole, 1,3,4-thiadiazole, pyridine, pyrimidine, pyrazine, pyridazine, 1,2,4-triazine or 1,3,5-triazine.

Optional substituents of the aromatic or heteroaromatic ring X include one or more of halogen, $C_{1-4}$ alkyl, $C_{3-6}$ cycloalkyl, $C_{2-4}$ alkenyl, $C_{2-4}$ alkynyl, $C_{2-4}$ alkynyloxy, phenyl, benzyloxy, cyano, isocyano, isothiocyanato, nitro, $NR^1R_2$, $NR^1OR^2$, $N_3$, $NHCOR^1$, $NR^1COR^2$, $NHCONR^1R^2 N=CHNR^1R^2$, $NHSO_2R^1$, $OR^1$, $OCOR^1$, $OSO_2R^1$, $SR^1$, $SOR^1$, $SO_2R^1$, $SO_2OR^1$, $SO_2NR^1R^2$, $COR^1$, $CR^1=NOR^2$, $CHR^1CO_2R^2$, $CO_2R^1$, $CONR^1R^2$, $CSNR^1R^2$, $CH_3O_2C.C:CH.OCH_3$, 1-(imidazol-1-yl)vinyl, a 5-membered heterocyclic ring containing one, two or three nitrogen heteroatoms, or a 5-or 6-membered heterocyclic ring containing one or two oxygen or sulphur heteroatoms, optionally a nitrogen heteroatom and optionally one or two oxo or thioxo substituents; or two substituents when ortho to one another, join to form a 5- or 6-membered aliphatic or aromatic ring optionally containing one or more oxygen, sulphur or nitrogen atoms. $R^1$ and $R^2$ are independently hydrogen, $C_{1-4}$ alkyl, $C_{2-4}$ alkenyl or phenyl. The aliphatic moieties of any of the substituents may themselves be substituted with one or more of halogen, cyano, $OR^1$, $SR^1$, $NR^1R^2$, $SiR^1{}_3$ or $OCOR^1$ and the phenyl moieties of any of the substituents may themselves be substituted with one or more of halogen, $C_{1-4}$ alkyl, $C_{1-4}$ alkoxy, nitro or cyano.

Typical optional substituents of the aromatic or heteroaromatic ring X are halogen, $C_{1-4}$ alkyl, $C_{3-6}$ cycloalkyl, $C_{2-4}$ alkenyl, $C_{2-4}$ alkynyl, $C_{2-4}$ alkenyloxy, $C_{2-4}$ alkynyloxy, phenyl, benzyloxy, cyano, isocyano, isothiocyanato, nitro, $NR^1R^2$, $NHCOR^1$, $NHCONR^1R^2$, $NHSO_2R^1$, $OR^1$, $OCOR^1$, $OSO_2R^1$, $SR^1$, $SOR^1$, $SO_2R^1$, $COR^1$, $CR^1=NOR^2$, $CO_2R^1$, $CONR^1R^2$, $CSNR^1R^2$. When substituents are ortho to one another, they may join to form a 5- or 6-membered aliphatic or aromatic ring optionally containing one or more oxygen, sulphur or nitrogen atoms. $R^1$ and $R^2$ are independently hydrogen, $C_{1-4}$ alkyl or phenyl. The aliphatic moieties of any of the substituents may themselves be substituted with one or more of halogen, cyano, $OR^1$ or $OCOR^1$ and the phenyl moieties of any of the substituents may themselves be substituted with one or more of halogen, $C_{1-4}$ alkyl, $C_{1-4}$ alkoxy, nitro or cyano.

Alkyl groups contain from 1 to 4 carbon atoms and may be in the form of straight or branched chains. Examples are methyl, ethyl, iso-propyl, n-butyl and t-butyl. Cycloalkyl groups contain from 3 to 6 carbon atoms and include cyclopropyl and cyclohexyl.

Alkenyl and alkynyl groups contain from 2 to 4 carbon atoms and may be in the form of straight or branched chains. Examples are ethenyl, allyl, methylallyl and propargyl.

Halogen is typically fluorine, chlorine or bromine.

Aliphatic moieties which may be substituted include, in particular, $C_{1-4}$ alkyl groups.

Of particular interest are compounds of formula (I) in which X is unsubstituted phenyl or phenyl substituted by halogen (especially chlorine), C1-4 alkyl, $C_{1-4}$ alkoxy, trifluoromethyl, cyano or nitro.

In one aspect the invention provides a compound of formula (I.1):

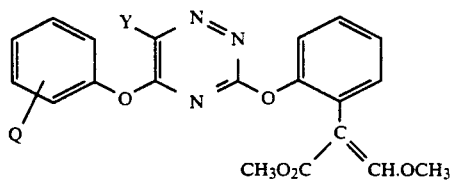

(I.1)

in which Y is H or chlorine and Q is H, halogen (especially chlorine), cyano, nitro or trifluoromethyl.

In another aspect the invention provides a compound of formula (I.2):

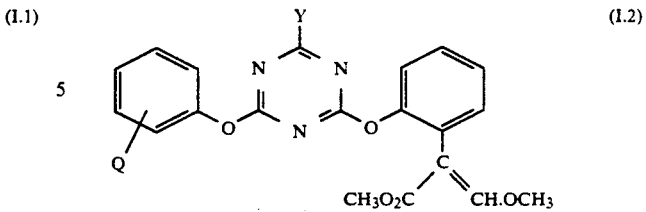

(I.2)

in which Y is H or chlorine and Q is halogen, $C_{1-4}$ alkyl, $C_{1-4}$ alkoxy (especially methoxy), cyano, nitro, trifluoromethyl or $CH_3O_2C.C:CH.OCH_3$.

The invention is illustrated by the compounds listed in Tables I to VI which follow. Throughout these Tables the methyl 3-methoxypropenoate group has the (E)-configuration.

TABLE I

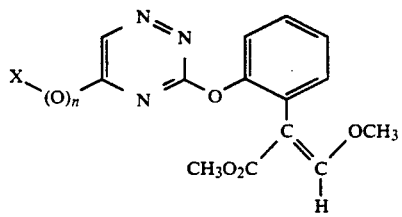

| Compound No. | X | n | Melting Point (°C.) | Olefinic* |
|---|---|---|---|---|
| 1 | $C_6H_5$— | 0 | 152–4 | 7.43 |
| 2 | 2-F—$C_6H_4$— | 0 | 106–108 | 7.44 |
| 3 | 3-F—$C_6H_4$— | 0 | | |
| 4 | 4-F—$C_6H_4$— | 0 | | |
| 5 | 2-Cl—$C_6H_4$— | 0 | | |
| 6 | 3-Cl—$C_6H_4$— | 0 | | |
| 7 | 4-Cl—$C_6H_4$— | 0 | 140–2 | 7.43 |
| 8 | 2-Br—$C_6H_4$— | 0 | | |
| 9 | 2-cyano-$C_6H_4$— | 0 | | |
| 10 | 3-cyano-$C_6H_4$— | 0 | | |
| 11 | 4-cyano-$C_6H_4$— | 0 | 65–70 | 7.42 |
| 12 | 2-isocyano-$C_6H_4$— | 0 | | |
| 13 | 2-$NO_2$—$C_6H_4$— | 0 | Gum | 7.48 |
| 14 | 3-$NO_2$—$C_6H_4$— | 0 | 160–2 | 7.44 |
| 15 | 4-$NO_2$—$C_6H_4$— | 0 | Foam | 7.42 |
| 16 | 2-$NH_2$—$C_6H_4$— | 0 | | |
| 17 | 3-NH($CH_3$)—$C_6H_4$— | 0 | | |
| 18 | 2-N($CH_3$)$_2$—$C_6H_4$— | 0 | | |
| 19 | 2-NH.CHO—$C_6H_4$— | 0 | | |
| 20 | 2-$CH_3$CO.NH—$C_6H_4$— | 0 | | |
| 21 | 3-$C_6H_5$CO.NH—$C_6H_4$— | 0 | | |
| 22 | 2-$H_2$N.CONH—$C_6H_4$— | 0 | | |
| 23 | 3-($C_2H_5$)NH.CONH—$C_6H_4$— | 0 | | |
| 24 | 2-$CH_3SO_2$NH—$C_6H_4$— | 0 | | |
| 25 | 3-$C_6H_5SO_2$NH—$C_6H_4$— | 0 | | |
| 26 | 2-HO—$C_6H_4$— | 0 | | |
| 27 | 3-HO—$C_6H_4$— | 0 | | |
| 28 | 4-HO—$C_6H_4$— | 0 | | |
| 29 | 2-$CH_3$O—$C_6H_4$— | 0 | | |
| 30 | 3-$CH_3$O—$C_6H_4$— | 0 | | |
| 31 | 4-$CH_3$O—$C_6H_4$— | 0 | | |
| 32 | 2-$C_2H_5$O—$C_6H_4$— | 0 | | |
| 33 | 3-(2-F—$C_6H_4$O)—$C_6H_4$— | 0 | | |
| 34 | 2-$CH_3CO_2$—$C_6H_4$— | 0 | | |
| 35 | 2-$CH_3SO_2$O—$C_6H_4$— | 0 | | |
| 36 | 3-(4-$CH_3$—$C_6H_4SO_2$O)—$C_6H_4$— | 0 | | |
| 37 | 2-thiocyanato-$C_6H_4$— | 0 | | |
| 38 | 3-thiocyanato-$C_6H_4$— | 0 | | |
| 39 | 4-thiocyanato-$C_6H_4$— | 0 | | |
| 40 | 2-$CH_3$S—$C_6H_4$— | 0 | | |
| 41 | 3-$CH_3$S—$C_6H_4$— | 0 | | |
| 42 | 4-$CH_3$S—$C_6H_4$— | 0 | | |
| 43 | 2-$CH_3$SO—$C_6H_4$— | 0 | | |
| 44 | 2-$CH_3SO_2$—$C_6H_4$— | 0 | | |
| 45 | 4-$CH_3(CH_2)_3SO_2$—$C_6H_4$— | 0 | | |
| 46 | 2-CHO—$C_6H_4$— | 0 | | |
| 47 | 3-CHO—$C_6H_4$— | 0 | | |

TABLE I-continued

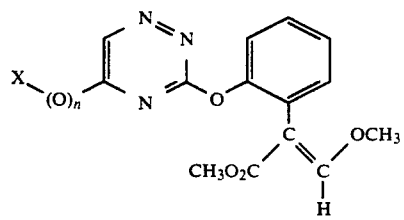

| Compound No. | X | n | Melting Point (°C.) | Olefinic* |
|---|---|---|---|---|
| 48 | 4-CHO—C$_6$H$_4$— | 0 | | |
| 49 | 2-CH$_3$CO—C$_6$H$_4$— | 0 | | |
| 50 | 3-C$_6$H$_5$CO—C$_6$H$_4$— | 0 | | |
| 51 | 2-(E)—HON:CH—C$_6$H$_4$— | 0 | | |
| 52 | 3-(E)—HON:CH—C$_6$H$_4$— | 0 | | |
| 53 | 4-(E)—HON:CH—C$_6$H$_4$— | 0 | | |
| 54 | 2-(E)—CH$_3$ON:CH—C$_6$H$_4$— | 0 | | |
| 55 | 2-(E)—HON:C(CH$_3$)—C$_6$H$_4$— | 0 | | |
| 56 | 2-H$_2$NCO—C$_6$H$_4$— | 0 | | |
| 57 | 3-H(CH$_3$)NCO—C$_6$H$_4$— | 0 | | |
| 58 | 4-(CH$_3$)$_2$NCO—C$_6$H$_4$— | 0 | | |
| 59 | 2-H$_2$NCS—C$_6$H$_4$— | 0 | | |
| 60 | 2-H(CH$_3$)NCS—C$_6$H$_4$— | 0 | | |
| 61 | 2-CH$_3$—C$_6$H$_4$— | 0 | | |
| 62 | 3-CH$_3$—C$_6$H$_4$— | 0 | | |
| 63 | 4-CH$_3$—C$_6$H$_4$— | 0 | | |
| 64 | 2-C$_2$H$_5$—C$_6$H$_4$— | 0 | | |
| 65 | 2-FCH$_2$—C$_6$H$_4$— | 0 | | |
| 66 | 2-BrCH$_2$—C$_6$H$_4$— | 0 | | |
| 67 | 2-ClCH$_2$—C$_6$H$_4$— | 0 | | |
| 68 | 2-cyanomethyl-C$_6$H$_4$— | 0 | | |
| 69 | 2-HOCH$_2$—C$_6$H$_4$— | 0 | | |
| 70 | 2-CH$_3$OCH$_2$—C$_6$H$_4$— | 0 | | |
| 71 | 2-CH$_3$CO$_2$CH$_2$—C$_6$H$_4$— | 0 | | |
| 72 | 3-cyanomethyl-C$_6$H$_4$— | 0 | | |
| 73 | 4-HOCH$_2$—C$_6$H$_4$— | 0 | | |
| 74 | 3-CH$_3$OCH$_2$—C$_6$H$_4$— | 0 | | |
| 75 | 2-CH$_2$:CH—C$_6$H$_4$— | 0 | | |
| 76 | 2-CH$_2$:CHCH$_2$—C$_6$H$_4$— | 0 | | |
| 77 | 2-HC≡C—C$_6$H$_4$— | 0 | | |
| 78 | 2-HC≡CCH$_2$—C$_6$H$_4$— | 0 | | |
| 79 | 3-CH$_2$:C(CH$_3$)CH$_2$—C$_6$H$_4$— | 0 | | |
| 80 | 2-CH$_2$:CHCH$_2$O—C$_6$H$_4$— | 0 | | |
| 81 | 2-HC≡CCH$_2$O—C$_6$H$_4$— | 0 | | |
| 82 | 2-C$_6$H$_5$—C$_6$H$_4$— | 0 | | |
| 83 | 3-C$_6$H$_5$—C$_6$H$_4$— | 0 | | |
| 84 | 4-C$_6$H$_5$—C$_6$H$_4$— | 0 | | |
| 85 | 2-C$_6$H$_5$O—C$_6$H$_4$— | 0 | | |
| 86 | 3-C$_6$H$_5$O—C$_6$H$_4$— | 0 | | |
| 87 | 4-C$_6$H$_5$O—C$_6$H$_4$— | 0 | | |
| 88 | 2-(4-Cl—C$_6$H$_4$O)—C$_6$H$_4$— | 0 | | |
| 89 | 2-C$_6$H$_5$CH$_2$O—C$_6$H$_4$— | 0 | | |
| 90 | 2-cyano-4-Cl—C$_6$H$_3$— | 0 | | |
| 91 | 2-NO$_2$-4-F—C$_6$H$_3$— | 0 | | |
| 92 | 2,4-di-Cl—C$_6$H$_3$— | 0 | | |
| 93 | 2,3-di-CH$_3$O—C$_6$H$_3$— | 0 | | |
| 94 | 2-cyano-5-Cl—C$_6$H$_3$— | 0 | | |
| 95 | 2,6-di-cyano-C$_6$H$_3$— | 0 | | |
| 96 | 2-F-5-Cl—C$_6$H$_3$— | 0 | | |
| 97 | 3,5-di-CH$_3$O—C$_6$H$_3$— | 0 | | |
| 98 | 3-cyano-4-F—C$_6$H$_3$— | 0 | | |
| 99 | 2-NO$_2$-3-CH$_3$O—C$_6$H$_3$— | 0 | | |
| 100 | 3-CH$_3$O-5-cyano-C$_6$H$_3$— | 0 | | |
| 101 | 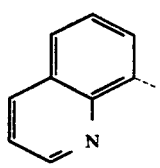 | 0 | | |

TABLE I-continued

[Structure: X(O)n-substituted 1,2,4-triazine linked via O to a phenyl bearing a C(=CH-OCH3)-CO2CH3 group]

| Compound No. | X | n | Melting Point (°C.) | Olefinic* |
|---|---|---|---|---|
| 102 | naphthalen-1-yl | 0 | | |
| 103 | naphthalen-2-yl | 0 | | |
| 104 | 2,3-methylenedioxy-C6H3— | 0 | | |
| 105 | benzo[b]thien-yl | 0 | | |
| 106 | benzimidazol-yl | 0 | | |
| 107 | Pyridin-2-yl | 0 | | |
| 108 | Pyridin-3-yl | 0 | | |
| 109 | Pyridin-4-yl | 0 | | |
| 110 | Pyrimidin-2-yl | 0 | | |
| 111 | Pyrimidin-4-yl | 0 | | |
| 112 | Pyrimidin-5-yl | 0 | | |
| 113 | Thien-2-yl | 0 | | |
| 114 | Thien-3-yl | 0 | | |
| 115 | C6H5— | 1 | 78–80 | 7.41 |
| 116 | 2-F—C6H4— | 1 | | |
| 117 | 3-F—C6H4— | 1 | | |
| 118 | 4-F—C6H4— | 1 | | |
| 119 | 2-Cl—C6H4— | 1 | | |
| 120 | 3-Cl—C6H4— | 1 | | |
| 121 | 4-Cl—C6H4— | 1 | | |
| 122 | 2-Br—C6H4— | 1 | | |
| 123 | 2-cyano-C6H4— | 1 | | |
| 124 | 3-cyano-C6H4— | 1 | | |
| 125 | 4-cyano-C6H4— | 1 | | |
| 126 | 2-isocyano-C6H4— | 1 | | |
| 127 | 2-NO2—C6H4— | 1 | | |
| 128 | 3-NO2—C6H4— | 1 | | |
| 129 | 4-NO2—C6H4— | 1 | | |
| 130 | 2-NH2—C6H4— | 1 | | |
| 131 | 3-NH(CH3)—C6H4— | 1 | | |
| 132 | 2-N(CH3)2—C6H4— | 1 | | |
| 133 | 2-NH.CHO—C6H4— | 1 | | |
| 134 | 2-CH3CO.NH—C6H4— | 1 | | |
| 135 | 3-C6H5CO.NH—C6H4— | 1 | | |
| 136 | 2-H2N.CONH—C6H4— | 1 | | |
| 137 | 3-(C2H5)NH.CONH—C6H4— | 1 | | |
| 138 | 2-CH3SO2NH—C6H4— | 1 | | |
| 139 | 3-C6H5SO2NH—C6H4— | 1 | | |
| 140 | 2-HO—C6H4— | 1 | | |
| 141 | 3-HO—C6H4— | 1 | | |
| 142 | 4-HO—C6H4— | 1 | | |
| 143 | 2-CH3O—C6H4— | 1 | | |

TABLE I-continued

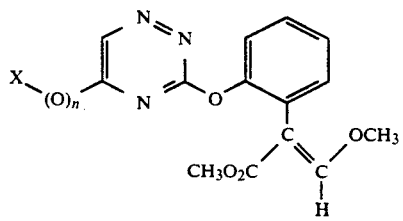

| Compound No. | X | n | Melting Point (°C.) | Olefinic* |
|---|---|---|---|---|
| 144 | 3-CH$_3$O—C$_6$H$_4$— | 1 | | |
| 145 | 4-CH$_3$O—C$_6$H$_4$— | 1 | | |
| 146 | 2-C$_2$H$_5$O—C$_6$H$_4$— | 1 | | |
| 147 | 3-(2-F—C$_6$H$_4$O)—C$_6$H$_4$— | 1 | | |
| 148 | 2-CH$_3$CO$_2$—C$_6$H$_4$— | 1 | | |
| 149 | 2-CH$_3$SO$_2$O—C$_6$H$_4$— | 1 | | |
| 150 | 3-(4-CH$_3$—C$_6$H$_4$SO$_2$O)—C$_6$H$_4$— | 1 | | |
| 151 | 2-thiocyanato-C$_6$H$_4$— | 1 | | |
| 152 | 3-thiocyanato-C$_6$H$_4$— | 1 | | |
| 153 | 4-thiocyanato-C$_6$H$_4$— | 1 | | |
| 154 | 2-CH$_3$S—C$_6$H$_4$— | 1 | | |
| 155 | 3-CH$_3$S—C$_6$H$_4$— | 1 | | |
| 156 | 4-CH$_3$S—C$_6$H$_4$— | 1 | | |
| 157 | 2-CH$_3$SO—C$_6$H$_4$— | 1 | | |
| 158 | 2-CH$_3$SO$_2$—C$_6$H$_4$— | 1 | | |
| 159 | 4-CH$_3$(CH$_2$)$_3$SO$_2$—C$_6$H$_4$— | 1 | | |
| 160 | 2-CHO—C$_6$H$_4$— | 1 | | |
| 161 | 3-CHO—C$_6$H$_4$— | 1 | | |
| 162 | 4-CHO—C$_6$H$_4$— | 1 | | |
| 163 | 2-CH$_3$CO—C$_6$H$_4$— | 1 | | |
| 164 | 3-C$_6$H$_5$CO—C$_6$H$_4$— | 1 | | |
| 165 | 2-(E)—HON:CH—C$_6$H$_4$— | 1 | | |
| 166 | 3-(E)—HON:CH—C$_6$H$_4$— | 1 | | |
| 167 | 4-(E)—HON:CH—C$_6$H$_4$— | 1 | | |
| 168 | 2-(E)—CH$_3$ON:CH—C$_6$H$_4$— | 1 | | |
| 169 | 2-(E)—HON:C(CH$_3$)—C$_6$H$_4$— | 1 | | |
| 170 | 2-H$_2$NCO—C$_6$H$_4$— | 1 | | |
| 171 | 3-H(CH$_3$)NCO—C$_6$H$_4$— | 1 | | |
| 172 | 4-(CH$_3$)$_2$NCO—C$_6$H$_4$— | 1 | | |
| 173 | 2-H$_2$NCS—C$_6$H$_4$— | 1 | | |
| 174 | 2-H(CH$_3$)NCS—C$_6$H$_4$— | 1 | | |
| 175 | 2-CH$_3$—C$_6$H$_4$— | 1 | | |
| 176 | 3-CH$_3$—C$_6$H$_4$— | 1 | | |
| 177 | 4-CH$_3$—C$_6$H$_4$— | 1 | | |
| 178 | 2-C$_2$H$_5$—C$_6$H$_4$— | 1 | | |
| 179 | 2-FCH$_2$—C$_6$H$_4$— | 1 | | |
| 180 | 2-BrCH$_2$—C$_6$H$_4$— | 1 | | |
| 181 | 2-ClCH$_2$—C$_6$H$_4$— | 1 | | |
| 182 | 2-cyanomethyl-C$_6$H$_4$— | 1 | | |
| 183 | 2-HOCH$_2$—C$_6$H$_4$— | 1 | | |
| 184 | 2-CH$_3$OCH$_2$—C$_6$H$_4$— | 1 | | |
| 185 | 2-CH$_3$CO$_2$CH$_2$—C$_6$H$_4$— | 1 | | |
| 186 | 3-cyanomethyl-C$_6$H$_4$— | 1 | | |
| 187 | 4-HOCH$_2$—C$_6$H$_4$— | 1 | | |
| 188 | 3-CH$_3$OCH$_2$—C$_6$H$_4$— | 1 | | |
| 189 | 2-CH$_2$:CH—C$_6$H$_4$— | 1 | | |
| 190 | 2-CH$_2$:CHCH$_2$—C$_6$H$_4$— | 1 | | |
| 191 | 2-HC≡C—C$_6$H$_4$— | 1 | | |
| 192 | 2-HC≡CCH$_2$—C$_6$H$_4$— | 1 | | |
| 193 | 3-CH$_2$:C(CH$_3$)CH$_2$—C$_6$H$_4$— | 1 | | |
| 194 | 2-CH$_2$:CHCH$_2$O—C$_6$H$_4$— | 1 | | |
| 195 | 2-HC≡CCH$_2$O—C$_6$H$_4$— | 1 | | |
| 196 | 2-C$_6$H$_5$—C$_6$H$_4$— | 1 | | |
| 197 | 3-C$_6$H$_5$—C$_6$H$_4$— | 1 | | |
| 198 | 4-C$_6$H$_5$—C$_6$H$_4$— | 1 | | |
| 199 | 2-C$_6$H$_5$O—C$_6$H$_4$— | 1 | | |
| 200 | 3-C$_6$H$_5$O—C$_6$H$_4$— | 1 | | |
| 201 | 4-C$_6$H$_5$O—C$_6$H$_4$— | 1 | | |
| 202 | 2-(4-Cl—C$_6$H$_4$O)—C$_6$H$_4$— | 1 | | |
| 203 | 2-C$_6$H$_5$CH$_2$O—C$_6$H$_4$— | 1 | | |
| 204 | 2-cyano-4-Cl—C$_6$H$_3$— | 1 | | |
| 205 | 2-NO$_2$-4-F—C$_6$H$_3$— | 1 | | |
| 206 | 2,4-di-Cl—C$_6$H$_3$— | 1 | | |
| 207 | 2,3-di-CH$_3$O—C$_6$H$_3$— | 1 | | |
| 208 | 2-cyano-5-Cl—C$_6$H$_3$— | 1 | | |
| 209 | 2,6-di-cyano-C$_6$H$_3$— | 1 | | |
| 210 | 2-F-5-Cl—C$_6$H$_3$— | 1 | | |
| 211 | 3,5-di-CH$_3$O—C$_6$H$_3$— | 1 | | |

TABLE I-continued

[Structure: triazine ring with X—(O)ₙ substituent, connected via O to phenyl group bearing CH₃O₂C—C=CH—OCH₃ (methyl methoxyacrylate) group]

| Compound No. | X | n | Melting Point (°C.) | Olefinic* |
|---|---|---|---|---|
| 212 | 3-cyano-4-F—C₆H₃— | 1 | | |
| 213 | 2-NO₂-3-CH₃O—C₆H₃— | 1 | | |
| 214 | 3-CH₃O-5-cyano-C₆H₃— | 1 | | |
| 215 | [quinoline-8-yl structure] | 1 | | |
| 216 | [naphthalen-1-yl structure] | 1 | | |
| 217 | [naphthalen-2-yl structure] | 1 | | |
| 218 | 2,3-methylenedioxy-C₆H₃ | 1 | | |
| 219 | [benzothiophene structure] | 1 | | |
| 220 | [benzimidazole structure] | 1 | | |
| 221 | Pyridin-2-yl | 1 | | |
| 222 | Pyridin-3-yl | 1 | | |
| 223 | Pyridin-4-yl | 1 | | |
| 224 | Pyrimidin-2-yl | 1 | | |
| 225 | Pyrimidin-4-yl | 1 | | |
| 226 | Pyrimidin-5-yl | 1 | | |
| 227 | Thien-2-yl | 1 | | |
| 228 | Thien-3-yl | 1 | | |
| 229 | 2,6-di-F—C₆H₃— | 1 | | |
| 230 | 2-n-C₃H₇—C₆H₄— | 1 | | |
| 231 | 2-CF₃—C₆H₄— | 1 | | |
| 232 | 2-i-C₃H₇—C₆H₄— | 1 | | |
| 233 | 2-n-C₃H₇O—C₆H₄— | 1 | | |
| 234 | 2-i-C₃H₇O—C₆H₄— | 1 | | |
| 235 | 2-n-C₄H₉O—C₆H₄— | 1 | | |
| 236 | 2-I—C₆H₄— | 1 | | |
| 237 | 2-n-C₅H₁₁—C₆H₄— | 1 | | |
| 238 | 2-i-C₄H₉O—C₆H₄— | 1 | | |
| 239 | 2-s-C₄H₉O—C₆H₄— | 1 | | |
| 240 | 2-t-C₄H₉O—C₆H₄— | 1 | | |
| 241 | 2-n-C₄H₉—C₆H₄— | 1 | | |
| 242 | 2-[(E)—CH₃O₂C.C=CH.OCH₃]—C₆H₄— | 1 | Gum | 7.43, 7.49 |
| 243 | 3-CF₃—C₆H₄— | 0 | 125-7 | 7.43 |
| 244 | 2-CH₃O-4-CH₃—C₆H₃— | 1 | | |

TABLE I-continued

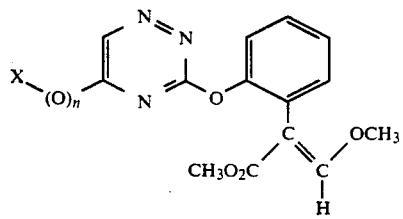

| Compound No. | X | n | Melting Point (°C.) | Olefinic* |
|---|---|---|---|---|
| 245 | 2,4-di-CH$_3$—C$_6$H$_3$— | 1 | | |
| 246 | 2,4,6-tri-CH$_3$—C$_6$H$_2$— | 1 | | |
| 247 | 2,6-di-CH$_3$—C$_6$H$_3$— | 1 | | |
| 248 | 2-F-6-CH$_3$O—C$_6$H$_3$— | 1 | | |
| 249 | 2-CH$_3$-4-Cl—C$_6$H$_3$— | 1 | | |
| 250 | C$_6$F$_5$— | 1 | | |
| 251 | 3,4-methylenedioxy-C$_6$H$_3$— | 1 | | |
| 252 | 3,4-di-Cl—C$_6$H$_3$— | 1 | | |
| 253 | 2-CH$_3$O-4-F—C$_6$H$_3$— | 1 | | |
| 254 | 3,4-di-CH$_3$—C$_6$H$_3$— | 1 | | |
| 255 | 2,3,5-tri-CH$_3$—C$_6$H$_2$— | 1 | | |
| 256 | 2,4-di-F—C$_6$H$_3$— | 1 | | |
| 257 | 2,4-di-Cl—C$_6$H$_3$— | 1 | | |
| 258 | 3,4,5-tri-CH$_3$—C$_6$H$_2$— | 1 | | |
| 259 | 3-cyanopyridin-2-yl | 0 | | |
| 260 | 5-CF$_3$-pyridin-2-yl | 0 | | |
| 261 | 2-CH$_3$-pyridin-3-yl | 0 | | |
| 262 | 2-Cl-pyridin-3-yl | 0 | | |
| 263 | 2-CH$_3$O-pyridin-4-yl | 0 | | |
| 264 | 5-Br-pyrimidin-2-yl | 0 | | |
| 265 | 5-F-pyrimidin-2-yl | 0 | | |
| 266 | 4-Cl-pyrimidin-2-yl | 0 | | |
| 267 | 2-phenylpyrimidin-5-yl | 0 | | |
| 268 | 6-Cl-pyrazin-2-yl | 0 | | |
| 269 | 6-Cl-pyridazin-3-yl | 0 | | |
| 270 | 3-cyanopyridin-2-yl | 1 | | |
| 271 | 5-CF$_3$-pyridin-2-yl | 1 | | |
| 272 | 2-CH$_3$-pyridin-3-yl | 1 | | |
| 273 | 2-Cl-pyridin-3-yl | 1 | | |
| 274 | 2-CH$_3$O-pyridin-4-yl | 1 | | |
| 275 | 5-Br-pyrimidin-2-yl | 1 | | |
| 276 | 5-F-pyrimidin-2-yl | 1 | | |
| 277 | 4-Cl-pyrimidin-2-yl | 1 | | |
| 278 | 2-phenylpyrimidin-5-yl | 1 | | |
| 279 | 6-Cl-pyrazin-2-yl | 1 | | |
| 280 | 6-Cl-pyridazin-3-yl | 1 | | |

*Chemical shift of singlet from olefinic proton on β-methoxypropenoate group (ppm from tetramethylsilane). Solvent: CDCl$_3$ unless otherwise stated.

TABLE II

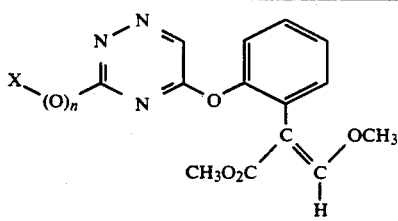

Table II comprises 280 compounds of the general structure above with all the values of X and n listed in Table I. That is, compounds numbers 1 to 280 of Table II are the same as those of Table I except that the 3- and 5-substituents of the 1,2,4-triazine ring in Table I are reversed in Table II.

TABLE II

| Compound No. | X | n | Melting Point (°C.) | Olefinic* |
|---|---|---|---|---|
| 115 | C$_6$H$_5$— | 1 | Foam | 7.48 |

TABLE II-continued

| Compound No. | X | n | Melting Point (°C.) | Olefinic* |
|---|---|---|---|---|
| 229 | 2,6-di-F—C$_6$H$_3$— | 1 | Gum | 7.50 |

*Chemical shift of singlet from olefinic proton on β-methoxypropenoate group (ppm from tetramethylsilane). Solvent: CDCl$_3$ unless otherwise stated.

TABLE III

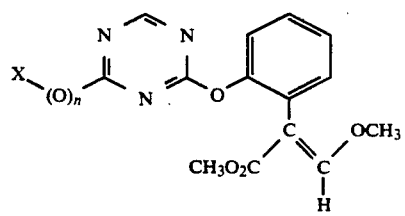

Table III comprises 280 compounds of the general structure above with all the values of X and n listed in Table I. That is, compounds numbers 1 to 280 of Table III are the same as those of Table I except that the triazine ring is a 3,5-disubstituted 1,2,4-triazine in Table I and a 2, 4-disubstituted 1,3,5-triazine in Table III.

TABLE III

| Compound No | X | n | Melting Point (°C.) | Olefinic* |
|---|---|---|---|---|
| 1 | $C_6H_5-$ | 0 | 142-3 | 7.46 |
| 115 | $C_6H_5-$ | 1 | 104-5 | 7.48 |
| 116 | $2\text{-}F-C_6H_4-$ | 1 | 96-101 | 7.48 |
| 119 | $2\text{-}Cl-C_6H_4-$ | 1 | 53-58 | 7.49 |
| 122 | $2\text{-}Br-C_6H_4-$ | 1 | 52-55 | 7.44 |
| 123 | $2\text{-cyano-}C_6H_4-$ | 1 | Foam | 7.51 |
| 143 | $2\text{-}CH_3O-C_6H_4-$ | 1 | 130.5-132.5 | 7.49 |
| 146 | $2\text{-}CH_3CH_2O-C_6H_4-$ | 1 | Foam | 7.48 |
| 175 | $2\text{-}CH_3-C_6H_4-$ | 1 | 120-1 | 7.48 |
| 178 | $2\text{-}C_2H_5-C_6H_4-$ | 1 | Gum | 7.47 |
| 211 | $3,5\text{-di-}CH_3O-C_6H_3-$ | 1 | Foam | 7.48 |
| 229 | $2,6\text{-di-}F-C_6H_3-$ | 1 | Gum | 7.48 |
| 230 | $2\text{-}\underline{n}\text{-}C_3H_7-C_6H_4-$ | 1 | 66-73 | 7.48 |
| 231 | $2\text{-}CF_3-C_6H_4-$ | 1 | 53-58 | 7.41 |
| 232 | $2\text{-}\underline{i}\text{-}C_3H_7-C_6H_4-$ | 1 | Foam | 7.48 |
| 234 | $2\text{-}\underline{i}\text{-}C_3H_7O-C_6H_4-$ | 1 | Foam | 7.47 |
| 242 | $2\text{-}[(\underline{E})\text{-}CH_3O_2C.C=CH.OCH_3]-C_6H_4-$ | 1 | 80-85 | 7.49 |
| 244 | $2\text{-}CH_3O\text{-}4\text{-}CH_3-C_6H_3-$ | 1 | 70-72 | 7.50 |
| 245 | $2,4\text{-di-}CH_3-C_6H_3-$ | 1 | Gum | 7.49 |
| 246 | $2,4,6\text{-tri-}CH_3-C_6H_3-$ | 1 | 74-76 | 7.49 |
| 247 | $2,6\text{-di-}CH_3-C_6H_3-$ | 1 | 62-64 | 7.49 |
| 248 | $2\text{-}F\text{-}6\text{-}CH_3O-C_6H_3-$ | 1 | 67-70 | 7.50 |
| 249 | $2\text{-}CH_3\text{-}4\text{-}Cl-C_6H_3-$ | 1 | 61-63 | 7.48 |
| 250 | $C_6F_5-$ | 1 | Gum | 7.49 |
| 251 | $3,4\text{-methylenedioxy-}C_6H_3-$ | 1 | Foam | 7.48 |
| 252 | $3,4\text{-di-}Cl-C_6H_3-$ | 1 | Foam | 7.48 |
| 254 | $3,4\text{-di-}CH_3-C_6H_3-$ | 1 | Foam | 7.48 |
| 255 | $2,3,5\text{-tri-}CH_3-C_6H_2-$ | 1 | 148.2-149.8 | 7.49 |
| 256 | $2,4\text{-di-}F-C_6H_3-$ | 1 | Foam | 7.49 |
| 257 | $2,4\text{-di-}Cl-C_6H_3-$ | 1 | Foam | 7.50 |
| 258 | $3,4,5\text{-tri-}CH_3-C_6H_2-$ | 1 | Foam | 7.49 |
| 261 | $2\text{-}CH_3\text{-pyridin-3-yl}$ | 1 | 147-9 | 7.48 |
| 262 | $2\text{-}Cl\text{-pyridin-3-yl}$ | 1 | Foam | 7.48 |

*Chemical shift of singlet from olefinic proton on β-methoxypropenoate group (ppm from tetramethylsilane). Solvent: CDCl₃ unless otherwise stated.

TABLE IV

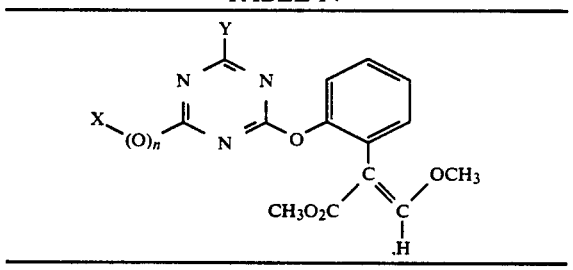

| Compound No | X | Y | n | Melting Point (°C.) | Olefinic* |
|---|---|---|---|---|---|
| 1 | $C_6H_5-$ | Cl | 1 | 73-75 | 7.47 |
| 2 | $2\text{-cyano-}C_6H_4-$ | Cl | 1 | 138-139 | 7.51 |
| 3 | $2\text{-}CH_3-C_6H_4-$ | Cl | 1 | 77-81 | 7.47 |
| 4 | $2\text{-}CH_3O-C_6H_4-$ | Cl | 1 | 57.5-65 | 7.48 |
| 5 | $2,6\text{-di-}F-C_6H_3-$ | Cl | 1 | Foam | 7.40 |
| 6 | $2\text{-}Br-C_6H_4-$ | Cl | 1 | 117-119 | 7.47 |
| 7 | $2\text{-}F-C_6H_4-$ | Cl | 1 | 48-50 | 7.50 |
| 8 | $2\text{-}C_2H_5-C_6H_4-$ | Cl | 1 | 65-70 | 7.46 |
| 9 | $2\text{-}NO_2-C_6H_4$ | Cl | 1 | 158-160 | 7.51 |
| 10 | $2\text{-}\underline{n}\text{-}C_3H_7-C_6H_4-$ | Cl | 1 | 41-45 | 7.47 |

*Chemical shift of singlet from olefinic proton on β-methoxypropenoate group (ppm from tetramethylsilane). Solvent: CDCl₃ unless otherwise stated.

TABLE V

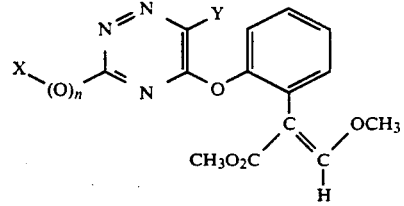

| Compound No | X | Y | n | Melting Point (°C.) | Olefinic* |
|---|---|---|---|---|---|
| 1 | $C_6H_5-$ | Cl | 1 | Gum | 7.50 |
| 2 | $2,6\text{-di-}F-C_6H_4-$ | Cl | 1 | Foam | 7.48 |
| 3 | $2\text{-}[(\underline{E})\text{-}CH_3O_2C.C=CH.OCH_3]-C_6H_4-$ | Cl | 1 | 73-75 | 7.42, 7.52 |

*Chemical shift of singlet from olefinic proton on β-methoxypropenoate group (ppm from tetramethylsilane). Solvent: CDCl₃ unless otherwise stated.

TABLE VI

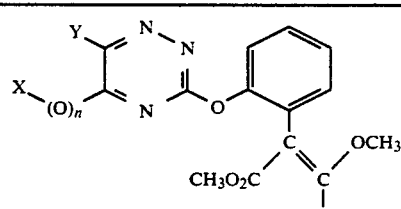

| Compound No | X | Y | n | Melting Point (°C.) | Olefinic* |
|---|---|---|---|---|---|
| 1 | $C_6H_5-$ | Cl | 1 | Oil | 7.41 |

*Chemical shift of singlet from olefinic proton on β-methoxypropenoate group (ppm from tetramethylsilane). Solevent: CDCl₃ unless otherwise stated.

TABLE VII: Selected Proton NMR Data

Table VII shows selected proton NMR data for compounds described in Tables I–VI. As indicated in Tables I–VI, chemical shifts are measured in ppm for tetramethylsilane and deuterochloroform was used as solvent. The NMR instrument operated at a frequency of 270 MHz. The following abbreviations are used:

s = singlet
d = doublet
t = triplet
q = quartet
m = multiplet
ppm = parts per million

| Compound No | Proton NMR data |
|---|---|
| 13 (Table I) | 3.56(3H,s); 3.70(3H,s); 7.28–7.45(4H,m); 7.48(1H,s); 7.62–7.82(3H,m); 8.06–8.11(1H,m); 9.11(1H,s) ppm. |
| 15 (Table I) | 3.51(3H,s); 3.64(3H,s); 7.32–7.48(5H,m, including 1H singlet at 7.42); 8.25–8.29 (2H,d); 8.35–8.39(2H,d); 9.53(1H.s) ppm. |
| 242 (Table I) | 3.55(3H,s); 3.60(3H,s); 3.70(3H,s); 3.72(3H,s); 7.17–7.41(8H,m); 7.43(1H,s); 7.49(1H,s); 8.64(1H.s) ppm. |
| 1 (Table II) | 3.61(3H,s); 3.72(3H.s); 7.11–7.45(9H,m); 7.48(1H,s); 8.71(1H,s) ppm. |
| 123 (Table III) | 3.64(3H,s); 3.73(3H,s); 7.10–7.48(6H,m); |

-continued

| Compound No | Proton NMR data |
|---|---|
| | 7.51(1H,s); 7.59-7.77(2H,m); 8.67(1H,s) ppm. |
| 146 (Table III) | 1.25(3H,t); 3.61(3H,s); 3.73(3H,s); 4.03(2H,q); 6.94-7.03(2H,m); 7.12-7.40(6H,m); 7.48(1H,s); 8.61(1H,s) ppm. |
| 178 (Table III) | 1.18(3H,t); 2.55(2H,q); 3.62(3H,s); 3.73(3H,s); 7.02-7.12(1H,m); 7.18-7.42(8H,m); 7.47(1H,s); 8.62(1H,s) ppm. |
| 229 (Table III) | 3.60(3H,s); 3.70(3H,s); 6.94-7.08(2H,t); 7.13-7.44(5H,m); 7.48(1H,s); 8.67(1H,s) ppm. |
| 232 (Table III) | 1.19(6H,d); 3.04(1H,septet); 3.61(3H,s); 3.74(3H,s); 7.01-7.09(1H,m); 7.18-7.41(7H,m); 7.48(1H,s); 8.63(1H,s) ppm. |
| 234 (Table III) | 1.21(6H,d); 3.62(3H,s); 3.73(3H,s); 4.52(1H,septet); 6.94-7.04(2H,m); 7.12-7.40(6H,m); 7.47(1H,s); 8.61(1H,s) ppm. |
| 241 (Table III) | 2.35(3H,s); 3.60(3H,s); 3.74(3H,s); 3.76(3H,s); 6.80(2H,d); 7.01(1H,d); 7.30(4H,m); 7.50(1H,s); 8.60(1H,s) ppm. |
| 245 (Table III) | 2.14(3H,s); 2.32(3H,s); 3.60(3H,s); 3.75(3H,s); 6.95(1H,d); 7.05(2H,m); 7.30(4H,m); 7.49(1H,s); 8.60(1H,s) ppm. |
| 246 (Table III) | 2.10(6H,s); 2.30(3H,s); 3.60(3H,s); 3.74(3H,s); 6.90(2H,s); 7.30(4H,m); 7.49(1H,s); 8.60(1H,s) ppm. |
| 247 (Table III) | 2.13(6H,s); 3.60(3H,s); 3.73(3H,s); 7.10(3H,s); 7.30(4H,m); 7.49(1H,s); 8.60(1H,s) ppm. |
| 248 (Table III) | 3.60(3H,s); 3.70(3H,s); 3.80(3H,s); 6.80(2H,m); 7.30(5H,m); 7.50(1H,s); 8.63(1H,s) ppm. |
| 249 (Table III) | 2.15(3H,s); 3.60(3H,s); 3.73(3H,s); 7.01(1H,d); 7.30(6H,m); 7.48(1H,s); 8.62(1H,s) ppm. |
| 250 (Table III) | 3.60(3H,s); 3.70(3H,s); 7.30(3H,m); 7.20(1H,d); 7.49(1H,s); 8.70(1H,s) ppm. |
| 251 (Table III) | 3.60(3H,s); 3.75(3H,s); 6.00(2H,s); 6.60(2H,m); 6.80(1H,d); 7.30(4H,m); 7.48(1H,s); 8.65(1H,s) ppm. |
| 252 (Table III) | 3.60(3H,s); 3.75(3H,s); 7.05(1H,dd); 7.20(1H,d); 7.35(4H,m); 7.45(1H,d); 7.48(1H,s); 8.65(1H,s) ppm. |
| 253 (Table III) | 3.62(3H,s); 3.74(3H,s); 3.76(6H,s); 6.33(2H,d); 6.40(1H,d); 7.35(4H,m); 7.48(1H,s); 8.65(1H,s) ppm. |
| 254 (Table III) | 2.25(6H,s); 3.60(3H,s); 3.75(3H,s); 6.90(2H,m); 7.15(1H,m); 7.35(4H,m); 7.48(1H,s); 8.62(1H,s) ppm. |
| 255 (Table III) | 2.00(3H,s); 2.27(3H,s); 2.29(3H,s); 3.60(3H,s); 3.73(3H,s); 6.75(1H,d); 6.92(1H,s); 7.25(1H,d); 7.35(3H,m); 7.29(1H,s); 8.60(1H,s) ppm. |
| 256 (Table III) | 3.60(3H,s); 3.72(3H,s); 6.95(2H,m); 7.20(1H,m); 7.35(4H,m); 7.49(1H,s); 8.65(1H,s) ppm. |
| 257 (Table III) | 3.60(3H,s); 3.75(3H,s); 7.30(6H,m); 7.49(1H,s); 7.50(1H,s); 8.65(1H,s) ppm. |
| 258 (Table III) | 2.15(3H,s); 2.30(6H,s); 3.62(3H,s); 3.75(3H,s); 6.80(2H,s); 7.30(4H,m); 7.49(1H,s); 8.62(1H,s) ppm. |
| 262 (Table III) | 3.63(3H,s); 3.74(3H,s); 7.14-7.42(6H,m); 7.48(1H,s); 7.59(1H,dd); 8.33-8.38(1H,m); 8.67(1H,s) ppm. |
| 5 (Table IV) | 3.63(3H,s); 3.73(3H,s); 6.94-7.14(2H,m); 7.15-7.38(3H,m); 7.40(1H,s) ppm. |
| 1 (Table V) | 3.66(3H,s); 3.78(3H,s); 7.09-7.42(9H,m); 7.50(1H,s) ppm. |
| 2 (Table V) | 3.62(3H,s); 3.72(3H,s); 6.90-7.10(2H,m); 7.10-7.50(5H,m); 7.50(1H,s); 8.78(1H,s) ppm. |

The compounds of the invention of formula (I) equivalent to (IA) when W is the group $CH_3O_2C.C=CH.OCH_3$] can be prepared by the steps shown in Schemes I, II and III. In these Schemes $X^1$ is an optionally substituted aromatic or heteroaromatic ring or a group which can be converted into such a ring; W is $CH_3O_2C.C=CH.OCH_3$ or a group that can be transformed into $CH_3O_2C.C=CH.OCH_3$ using methods previously described such as in EP-A-0242081; $Z^1$ and $Z^2$ (which may be the same or different) are leaving groups (such as halogen or $CH_3SO_2-$), $Z^1$ being the leaving group which is more readily displaced if (a) both $Z^1$ and $Z^2$ are present in the same compound or (b) if $Z^1$ and $Z^2$ are both present in different compounds of a coupling reaction; T is hydrogen or a metal (such as sodium) and any two of K, L and M are nitrogen and the other is CY (or a group that can be converted into CY, such as C-halogen which can be converted into CH). The reactions shown in Schemes I-III are performed either in a suitable solvent or without a solvent, and at a suitable temperature.

Thus compounds of the invention of formula (IA, n=0) can be prepared by treatment of substituted triazines of general formula (III) with phenols of formula (II) (wherein W is as defined above and T is hydrogen) in the presence of a base (such as potassium carbonate) (Scheme I).

Alternatively, compounds of formula (IA, n=0) can be prepared by treatment of substituted triazines of general formula (III) with phenolate salts of formula (II) (wherein W is as defined above and T is a metal, such as sodium).

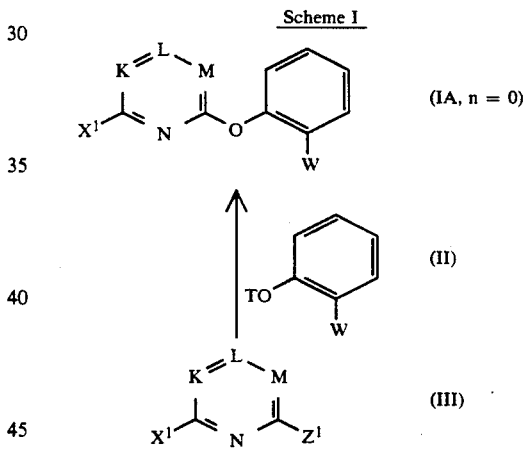

Scheme I

Compounds of the invention of formula [(IA, n=1): W is the group $CH_3O_2C.C=CH.OCH_3$]can be prepared by two successive reactions of the Ullmann type, using appropriately functionalised benzene and triazine intermediates. The pathways shown in Schemes II and III illustrate that the order of the steps by which these benzene and triazine units are assembled can be varied.

For example, compounds of formula (IA, n=1) can be prepared from compounds of formula (IV) by treatment with phenols of formula (V), wherein T is hydrogen, in the presence of a base (such as potassium carbonate). Alternatively, compounds of formula (IA, n=1) can be prepared from compounds of formula (IV) by treatment with phenolate salts of formula (V), wherein T is a metal (such as sodium) (Scheme II).

Compounds of formula (IV) can be prepared by treatment of compounds of formula (VI) with phenols of formula (II), wherein T is hydrogen, in the presence of a base (such as potassium carbonate). Alternatively, compounds of formula (IV) can be prepared by treatment of compounds of formula (VI) with phenolate salts of formula (II), wherein T is a metal (such as sodium).

Compounds of formula (IA, n=1) can also be prepared by treatment of compounds of formula (VII) with phenols of formula (II), wherein T is hydrogen, in the presence of a base (such as potassium carbonate). Alternatively, compounds of formula (IA, n=1) can be prepared by treatment of compounds of formula (VII) with phenolate salts of formula (II), wherein T is a metal (such as sodium) (Scheme III).

Compounds of formula (VII) can be prepared by treatment of triazines of formula (VIII) with compounds of formula (V), wherein T is hydrogen, in the presence of a base (such as potassium carbonate). Alternatively, compounds of formula (VII) can be prepared by treatment of triazines of formula (VIII) with compounds of formula (V), wherein T is a metal (such as sodium).

In some instances it is advantageous to use intermediates (IV) wherein $Z^2$ is the group 2-W-C$_6$H$_4$O, this group functioning as the leaving group on reaction with the compound (V). These intermediates (IV) wherein $Z^2$ is 2-W-C$_6$H$_4$O may be prepared by treatment of triazines (VI) with an excess of compound (II). Similarly, intermediates (VII) in which $Z^2$ is $X^1$O may be used, the group $X^1$O functioning as the leaving group on reaction with the phenol or phenolate (II). These intermediates (VII) wherein $Z^2$ is $X^1$O may be prepared by treatment of triazines (VIII) with an excess of compound (V).

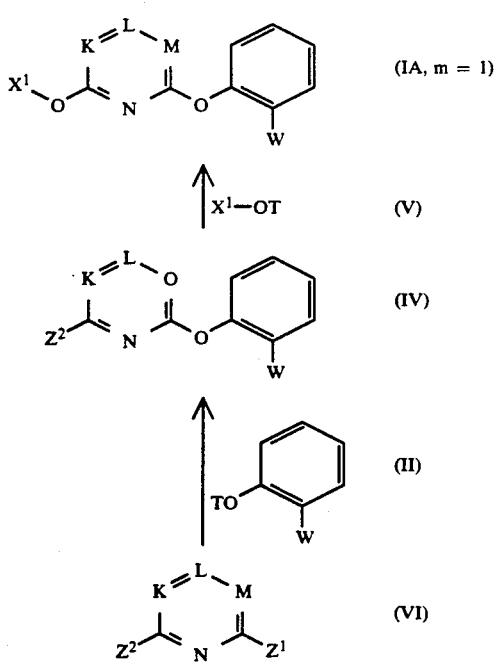

Scheme II

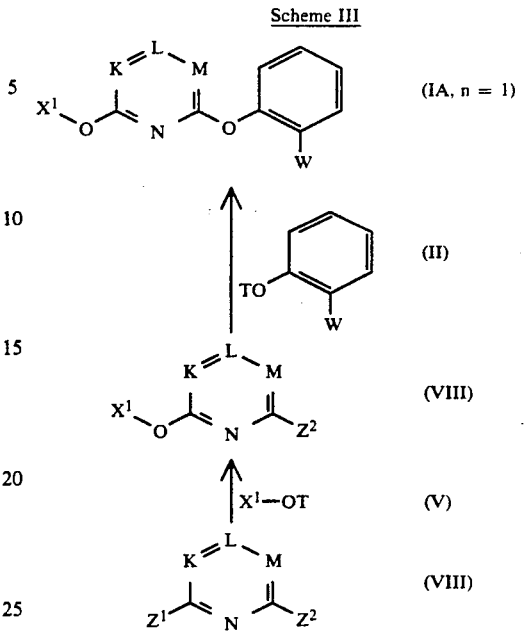

Scheme III

The last stage of the synthesis of the compounds of the invention may therefore be one of the following:

(i) construction of the group CH$_3$O$_2$C.C=CH.OCH$_3$ [in which case the group W in the compounds (II) and (IA) represents an appropriate precursor to the group CH$_3$O$_2$C.C=CH.OCH$_3$ during the coupling reaction shown in Scheme I]; or (ii) the final coupling reactions shown in Schemes I-III [in which case the group W in the intermediate (II) represents the group CH$_3$O$_2$C.C=CH.OCH$_3$]; or (iii) modification to the group $X^1$, either to convert it into an aromatic or heteroaromatic ring or, if it is already such a ring, to modify a substituent on it; or (iv) removal of a substituent (such as halogen) from the triazine ring of (IA) to afford a triazine wherein any two of K, L and M are nitrogen and the other is CH.

Triazines of formulae (III), (VI) and (VIII) and compounds of formula (V) can be prepared by standard methods described in the chemical literature. Compounds of formula (II) can either be prepared by standard methods described in the chemical literature, or when W is CH$_3$O$_2$C.C=CH.OCH$_3$, can be prepared by methods described in EP-A-0242081.

In a further aspect, the invention provides processes as herein described for preparing the compounds of the invention.

The compounds of the invention are active fungicides and may be used to control one or more of the following pathogens: *Pyricularia oryzae* on rice. *Puccinia recondita, Puccinia striiformis* and other rusts on wheat, *Puccinia hordei, Puccinia striiformis* and other rusts on barley, and rusts on other hosts e.g. coffee, pears, apples, peanuts, vegetables and ornamental plants. *Erysiphe graminis* (powdery mildew) on barley and wheat and other powdery mildews on various hosts such as *Sphaerotheca macularis* on hops, *Sphaerotheca fuliginea* on cucurbits (e.g. cucumber), *Podosphaera leucotricha* on apple and *Uncinula necator* on vines. *Helminthosporium* spp., *Rhynchosporium* spp., *Septoria* spp., *Pyrenophora* spp., *Pseudocercosporella herpotrichoides* and *Gaeumannomyces graminis* on cereals. *Cercospora arachidicola* and

*Cercosporidium personata* on peanuts and other *Cercospora* species on other hosts, for example, sugar beet, bananas, soya beans and rice. *Botrytis cinerea* (grey mould) on tomatoes, strawberries, vegetables, vines and other hosts. *Alternaria* spp. on vegetables (e.g. cucumber), oil-seed rape, apples, tomatoes and other hosts. *Venturia inaequalis* (scab) on apples. *Plasmopara viticola* on vines. Other downy mildews such as *Bremia lactucae* on lettuce, *Peronospora* spp. on soybeans, tobacco, onions and other hosts, *Pseudoperonospora humuli* on hops and *Pseudoperonospora cubensis* on cucurbits. *Phytophthora infestans* on potatoes and tomatoes and other *Phytophthora* spp. on vegetables, strawberries, avocado, pepper, ornamentals, tobacco, cocoa and other hosts. *Thanatephorus cucumeris* on rice and other *Rhizoctonia* species on various hosts such as wheat and barley, vegetables, cotton and turf.

Some of the compounds show a broad range of activities against fungi in vitro. They may also have activity against various post-harvest diseases of fruit (e.g. *Penicillium digitatum* and *italicum* and *Trichoderma viride* on oranges, *Gloeosporium musarum* on bananas and *Botrytis cinerea* on grapes).

Further, some of the compounds may be active as seed dressings against *Fusarium* spp., *Septoria* spp., *Tilletia* spp., (bunt, a seed-borne disease of wheat), *Ustilago* spp. and *Helminthosporium* spp. on cereals, *Rhizoctonia solani* on cotton and *Pyricularia oryzae* on rice.

The compounds may move acropetally/locally in plant tissue. Moreover, the compounds may be volatile enough to be active in the vapour phase against fungi on the plant.

The invention therefore provides a method of combating fungi which comprises applying to a plant, to a seed of a plant or to the locus of the plant or seed a fungicidally effective amount of a compound as hereinbefore defined, or a composition containing the same.

The compounds may be used directly for agricultural purposes but are more conveniently formulated into compositions using a carrier or diluent. The invention thus provides fungicidal compositions comprising a compound as hereinbefore defined and an acceptable carrier or diluent therefor.

The compounds can be applied in a number of ways. For example, they can be applied, formulated or unformulated, directly to the foliage of a plant, to seeds or to other medium in which plants are growing or are to be planted, or they can be sprayed on, dusted on or applied as a cream or paste formulation, or they can be applied as a vapour or as slow release granules.

Application can be to any part of the plant including the foliage, stems, branches or roots, or to soil surrounding the roots, or to the seed before it is planted, or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic and eradicant treatments.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example, fillers such as kaolin, bentonite, kieselguhr, dolomite, calcium carbonate, talc, powdered magnesia, fullers earth, gypsum, diatomaceous earth and china clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example, a mineral oil) for assisting the adhesion of the composition to the seed; alternatively the active ingredient can be formulated for seed dressing purposes using an organic solvent (for example, N-methylpyrrolidone, propylene glycol or dimethylformamide). The compositions may also be in the form of wettable powders or water dispersible granules comprising wetting or dispersing agents to facilitate the dispersion in liquids. The powders and granules may also contain fillers and suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as isophorone, cyclohexanone, and methylcyclohexanone, chlorinated hydrocarbons such as chlorobenzene and trichlorethane, and alcohols such as benzyl alcohol, furfuryl alcohol, butanol and glycol ethers.

Suspension concentrates of largely insoluble solids may be prepared by ball or bead milling with a dispersing agent with a suspending agent included to stop the solid settling.

Compositions to be used as sprays may be in the form of aerosols wherein the formulation is held in a container under pressure of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The invention compounds can be used as mixtures with fertilizers (e.g. nitrogen-, potassium- or phosphorus-containing fertilizers). Compositions comprising only granules of fertilizer incorporating, for example coated with, the compound are preferred. Such granules suitably contain up to 25% by weight of the compound. The invention therefore also provides a fertilizer composition comprising a fertilizer and the compound of general formula (I) or a salt or metal complex thereof.

Wettable powders, emulsifiable concentrates and suspension concentrates will normally contain surfactants, e.g. a wetting agent, dispersing agent, emulsifying agent or suspending agent. These agents can be cationic, anionic or non-ionic agents.

Suitable cationic agents are quaternary ammonium compounds, for example, cetyltrimethylammonium bromide. Suitable anionic agents are soaps, salts of aliphatic monoesters of sulphuric acid (for example, sodium lauryl sulphate), and salts of sulphonated aromatic compounds (for example, sodium dodecylbenzenesulphonate, sodium, calcium or ammonium lignosulphonate, butylnaphthalene sulphonate, and a mixture of sodium diisopropyl- and triisopropyl- naphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example, polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10-85%, for example 25-60%, by weight of the active ingredient. After dilution to form aqueous preparations, such preparations may contain varying amounts of the active ingredient depending upon the intended purpose, but an aqueous preparation containing 0.0005% or 0.01% to 10% by weight of active ingredient may be used.

The compositions of this invention may contain other compounds having biological activity, e.g. compounds having similar or complementary fungicidal activity or which possess plant growth regulating, herbicidal or insecticidal activity.

A fungicidal compound which may be present in the composition of the invention may be one which is capable of combating ear diseases of cereals (e.g. wheat) such as Septoria, Gibberella and Helminthosporium spp., seed and soil-borne diseases and downy and powdery mildews on grapes and powdery mildew and scab on apple, etc. By including another fungicide, the composition can have a broader spectrum of activity than the compound of general formula (I) alone. Further the other fungicide can have a synergistic effect on the fungicidal activity of the compound of general formula (I). Examples of fungicidal compounds which may be included in the composition of the invention are (RS)-1-aminopropylphosphonic acid, (RS)-4-(4-chlorophenyl)-2-phenyl-2-(1H-1,2,4-triazol-1methyl)butyronitrile, (Z)-N-but-2-enyloxymethyl-2-chloro-2',6'-diethylacetanilide, 1-(2-cyano-2-metho acetyl)-3-ethyl urea, 1-[(2RS,4RS;2RS,4RS)-4-bromo-2-(2,4-dichlorophenyl)-tetrahydrofu azole, 3-(2,4-dichlorophenyl)-2-(1H-1,2,4-triazol-1-yl)-quinazolin-4(3H)-one, 3-chloro-4-triazol-1-methyl)-1,3-dioxolan-2-yl]phenyl-4-chlorophenyl ether, 3-chloro-5-ethylsulphinylthiophene-2,4-dicarbonitrile, 4-bromo-2-cyano-N,N-dimethyl-6-trifluoromethy imidazole-1-sulphonamide, 5-ethyl-5,8-dihydro-8-oxo(1,3)-0 -dioxolo(4,5-g)quinoline-7-carboxyli -chloro-2,6-xylyl)-2-methoxyacetamido]-butyrolactone, anilazine, benalaxyl, benomyl, biloxazol, binapacryl, biter-
tanol, blasticidin S, bupirimate, buthiobate, captafol, captan, carbendazim, carboxin, chlorbenzthiazone, chloroneb, chlorothalonil, chlorozolinate, copper containing compounds such as copper oxychloride, copper sulphate and Bordeaux mixture, cycloheximide, cymoxanil, cyproconazole, cyprofuram, di-2-pyridyl disulphide 1,1'-dioxide, dichlofluanid, dichlone, diclobutrazol, diclomezine, dicloran, difenoconazole, dimethamorph, dimethirimol, diniconazole, dinocap, ditalimfos, dithianon, dodemorph, dodine, edifenphos, etaconazole, ethirimol, ethyl (Z)-N-benzyl-N-([methyl(-methylthioethylideneamino-oxycarbonyl)amino]thio)-β-alaninate, etridiazole, fenapanil, fenarimol, fenfuram, fenpiclonil, fenpropidin, fenpropimorph, fentin acetate, fentin hydroxide, flutolanil, flutriafol, fluzilazole, folpet, fosetyl-aluminium, fuberidazole, furalaxyl, furconazole-cis, guazatine, hexaconazole, hydroxyisoxazole, imazalil, imibenconazole, iprobenfos, iprodione, isoprothiolane, kasugamycin, mancozeb, maneb, mepronil, metalaxyl, methfuroxam, metsulfovax, myclobutanil, N-(4-methyl-6-prop-1-ynylpyrimidin-2-yl)aniline, neoasozin, nickel dimethyldithiocarbamate, nitrothal-isopropyl, nuarimol, ofurace, organomercury compounds, oxadixyl, oxycarboxin, pefurazoate, penconazole, pencycuron, phenazin oxide, phthalide, polyoxin D, polyram, probenazole, prochloraz, procymidone, propamocarb, propiconazole, propineb, prothiocarb, pyrazophos, pyrifenox, pyroquilon, pyroxyfur, pyrrolnitrin, quinomethionate, quintozene, streptomycin, sulphur, techlofthalam, tecnazene, tebuconazole, tetraconazole, thiabendazole, thiophanate-methyl, thiram, tolclofos-methyl, triacetate salt of 1,1'-iminodi(octamethylene)-diguanidine, triadimefon, triadimenol, triazbutyl, tricyclazol,, tridemorph, triforine, validamycin A, vinclozolin, zarilamid and zineb. The compounds of general formula (I) can be mixed with soil, peat or other rooting media for the protection of plants against seed-borne, soil-borne or foliar fungal diseases.

Suitable insecticides which may be incorporated in the composition of the invention include buprofezin, carbaryl, carbofuran, carbosulfan, chlorpyrifos, cycloprothrin, demeton-s-methyl, diazinon, dimethoate, ethofenprox, fenitrothion, fenobucarb, fenthion, formothion, isoprocarb, isoxathion, monocrotophos, phenthoate, pirimicarb, propaphos and XMC.

Plant growth regulating compounds are compounds which control weeds or seedhead, formation, or selectively control the growth of less desirable plants (e.g. grasses).

Examples of suitable plant growth regulating compounds for use with the invention compounds are 3,6-dichloropicolinic acid, 1-(4-chlorophenyl)-4,6-dimethyl-2-oxo-1,2-dihydropyridine-3-carboxylic ac methyl-3,6-dichloroanisate, abscisic acid, asulam, benzoylpropethyl, carbetamide, daminozide, difenzoquat, dikegulac, ethephon, fenpentezol, fluoridamid, glyphosate, glyphosine, hydroxybenzonitriles (e.g. bromoxynil), inabenfide, isopyrimol, long chain fatty alcohols and acids, maleic hydrazide, mefluidide, morphactins (e.g. chlorfluoroecol), paclobutrazol, phenoxyacetic acids (e.g. 2,4-D or MCPA), substituted benzoic acid (e.g. triiodobenzoic acid), substituted quaternary ammonium and phosphonium compounds (e.g. chloromequat, chlorphonium or mepiquatchloride), tecnazene, the auxins (e.g. indoleacetic acid, indolebutyric acid, naphthylacetic acid or naphthoxyacetic acid), the cytokinins (e.g. benzimidazole, benzyladenine, benzylaminopurine, diphenylurea or kinetin), the gibberellins (e.g. $GA_3$, $GA_4$ or $GA_7$) and triapenthenol.

The following Examples illustrate the invention. In the Examples, the term 'ether' refers to diethyl ether, anhydrous magnesium sulphate was used to dry solutions, and solutions were concentrated under reduced pressure. Reactions involving air- or water-sensitive intermediates were performed under an atmosphere of nitrogen and solvents were dried before use, where appropriate. Unless otherwise stated, chromatography was performed on a column of silica gel as the stationary phase. NMR data are selective; no attempt is made to list every absorption in all cases. $^1$H NMR spectra were recorded using $CDCl_3$-solutions. The following abbreviations are used:

| | |
|---|---|
| DMSO | = dimethylsulphoxide |
| DMF | = N,N-dimethylformamide |
| NMR | = nuclear magnetic resonance |
| IR | = infrared |
| GC | = Gas chromatography |
| s | = singlet |
| d | = doublet |
| m | = multiplet |
| mp | = melting point |
| ppm | = parts per million |

EXAMPLE 1

This Example illustrates the preparation of (E)-methyl 2-[2-(5-(4-chlorophenyl)-1,2,4-triazin-3--yloxy)phenyl]-3-methoxypropenoate (Compound Table I).

To a stirred solution of (E)-methyl 2-(2-hydroxyphenyl)-3-methoxypropenoate (0.44g, 2.1mmol; prepared as described in Example 3 of EP-A-0242081) and anhydrous potassium carbonate (0.276g, 2.0mmol) in dry DMF (5ml) at 0°-2° C. under nitrogen was added drop-wise over 10 minutes a solution of 5-(4-chlorophenyl)-3-methylsulphonyl-1,2,4-triazine (0.54g, 2.0mmol; prepared as described by E. C. Taylor, J. E. Macor and J. L. Pont in *Tetrahedron*, 1987, 43, 5145) in dry DMF (5ml). The reaction mixture was stirred for 15 minutes and then allowed to warm to ambient temperature. After 1 hour, a further amount of the sulphone (0.11 g) was added. The reaction mixture was then stirred at ambient temperature for 1 hour, poured into water and extracted into ether (x3). The combined yellow ether extracts were washed with dilute sodium hydroxide solution (x3) and water (x3) and then dried. The ether was removed under reduced pressure to give a yellow solid (0.46g). Trituration with ether and filtration afforded the title compound as a pale yellow solid (0.374g); m.p. 140°-2° C.; IR maxima 1721, 1621 cm$^{-1}$; $^1$H NMR (CDCl$_3$) δ3.51(3H,s); 3.71(3H,s); 7.29-7.47 (5H,m, including a 1H singlet at 7.43); 7.48-7.52(2H,d); 8.02-8.06 (2H,d); 9.03(1H,s)ppm.

EXAMPLE 2

This Example illustrates the preparation of (E)-methyl 2-[2-(4-phenyl-1,3,5-triazin-2-yloxy)phenyl]-3-methoxypropenoate (Compound No. 1 of Table III).

To a stirred solution of (E)-methyl 2-(2-hydroxyphenyl)-3-methoxypropenoate (0.458g, 2.2mmol; prepared as described in Example 3 of EP-A-0242081) and anhydrous potassium carbonate (276mg, 2.0mmol) in dry DMF (5ml) at 0°-2° C. under nitrogen was added drop-wise over 5 minutes a solution of 2-chloro-4-phenyl-1,3,5-triazine (383mg, 2.0mmol; prepared as described by R. L. N. Harris in *Synthesis*, 1980, 841) in dry DMF (5ml). The reaction mixture was stirred for 3.75 hours and then allowed to warm to ambient temperature. Water was added and the white precipitate which formed was extracted into ethyl acetate (x3). The combined organic extracts were washed with dilute sodium hydroxide solution (x2) and water (x3) and then dried. The ether was removed under reduced pressure to give a sticky, pale yellow solid. Trituration with petrol followed by filtration then afforded the title compound as a cream-colored solid (0.49g); m.p. 142°-3° C.; IR maxima 1710, 1631 cm$^{-1}$; $^1$H NMR (CDCl$_3$) δ6 3.55(3H,s); 3.68(3H,s); 7.28-7.62(8H,m, including a 1H singlet at 7.46); 8.40-8.44(2H,d); 8.95 (1H,s)ppm.

EXAMPLE 3

This Example illustrates the preparation of (E)-methyl 2-[2-(4-phenoxy-1,3,5-triazin-2-yloxy) phenyl]-3-methoxypropenoate (Compound No. 115 of Table III).

A mixture containing (E)-methyl 2-(2-hydroxyphenyl) -3-methoxypropenoate (2.58g, 12.40 mmol), 2,4-dichlo -phenoxy-1,3,5-triazine (3.00g, 12.40 mmol), anhydrous potassium carbonate (1.71g, 12.40 mmol) and 4Å molecular sieves in dry THF (60ml) was stirred at room temperature for two days. The cloudy reaction mixture was diluted with water (50ml) and then extracted with dichloromethane (2×60ml) (an emulsion formed which was dispersed by filtration through celite). The combined organic extracts were dried and evaporated to give a pale yellow oil (5.68g). Chromatography (eluent ether-n-hexane, 1:1) afforded a white foam (3.79g) which was recrystallised from ether-n-hexane at low temperature to give (E)-methyl 2-[2-(4-chloro-6-phenoxy-1,3,5-triazin-2-yloxy)phenyl]-3-methoxypropenoate as a white powder (3.10g, 60%); m.p. 103°-4° C.

(E)-Methyl 2-[2-(4-chloro-6-phenoxy-1,3,5-triazin-2-yloxy)phenyl]-3-methoxypropenoate (2.0 stirred at room temperature over the weekend with sodium hypophosphite (NaH$_2$PO$_2$, 1.28g, 14.51 mmol), potassium carbonate (2.30g, 16.66 mmol) and 5% palladium on carbon (0.30g) in THF (45ml) and water (15ml). The reaction mixture was filtered through celite which was washed well with dichloromethane and water. The organic layer was separated, and the aqueous layer further extracted with dichloromethane. The combined organic layers were dried and evaporated to give a colourless oil (1.79g). Chromatography (eluent ether-n-hexane, 2:1) gave a white solid (0.88g) which on recrystallisation from ether (containing a trace of dichloromethane) and n-hexane afforded the title compound as a white powder (0.78g, m.p. 104°-5° C.; IR maxima 1694, 1638 cm$^{-1}$; mass spectrum m/e 379 (M+); $^1$H NMR (CDCl$_3$) δ3.63(3H,s); 3.75(3H,s); 7.13-7.50(9H,m); 7.48(1H,s); and 8.64(1H,s) ppm.

EXAMPLE 4

This Example illustrates the preparation of (E)-methyl 2-[2-(4-(2-bromophenoxy)-1,3,5-triazin-2-yloxy)phenyl]-3-methoxypropenoate (Compound Table III).

To a stirred solution of 2,6-dichloro-1,3,5-triazine (0.3g, 2 mmol; made according to R L N Harris, *Synthesis*, 1981, 907) and potassium carbonate (0.28g, 2 mmol) in dry acetonitrile (25 ml) at 0° C. under an atmosphere of nitrogen was added dropwise a solution of (E)- methyl 2-(2-hydroxyphenyl)-3-methoxypropenoate (0.42g, 2mmol) in dry acetonitrile (7 ml). Anhydrous caesium fluoride (0.30g, 2 mmol) and a catalytic amount of 18-crown-6 were added with stirring and the temperature was allowed to rise to room temperature. After stirring overnight, the reaction mixture was filtered and evaporated to leave a yellow/orange paste. Chromatography (eluent diethyl ether) afforded (E)-methyl 2-[2-(4-chloro-1,3,5-triazin-2-yloxy)phenyl]-3-methoxypropenoate (0.42 white solid, m.p. 137°-140° C.; Infrared max. 1704, 1631 cm$^{-1}$; $^1$H NMR (CDCl$_3$) $\delta$63.63(3H,s); 3.75(3H,s); 7.19-7.29(1H,m); 7.31-7.45(3H,m); 7.47(1H,s); 8.74(1H,s) ppm.

2-Bromophenol (0.14g, 0.787 mmol) and potassium carbonate (0.11 g, 0.787 mmol) were heated together in dry DMF (20 ml) under nitrogen for 15 minutes. A solution of (E)-methyl 2-[2-(4-chloro-1,3,5-triazin-2-yloxy)phenyl]-3-methoxypropenoate (0.23g, 0.712 catalytic amount of copper(I) chloride were added and the resulting mixture stirred at 60° C. for 2 hours. The reaction mixture was poured into water and then extracted with ether (x3). The combined ether extracts were washed with brine, dilute aqueous sodium hydroxide solution (x2) and water (x3) and then dried. Evaporation of the solvent gave a yellow gum (0.22g) which was chromatographed (eluent diethyl ether) to afford the title compound as a white powder (0.13g); m.p. 52°-55° C.; Infrared max. 1709, 1632 cm$^{-1}$; $^1$H NMR (CDCl$_3$) $\delta$3.63(3H,s); 3.74(3H,s); 7.14-7.44(7H,m); 7.48(1H,s); 7.66(1H,dd); 8.65(1H,s) ppm.

EXAMPLE 5

This Example illustrates the preparation of (E)-methyl 2-[2-(4,6-dichloro-1,3,5-triazin-2-yloxy)phenyl]-3-methoxypropenoate, an intermediate for synthesis of compounds of the invention.

To a stirred mixture containing cyanuric chloride (1.85g, 10 mmol), potassium carbonate (1.38g, 10 mmol) and molecular sieves in dry THF (40 ml) at room temperature was added a solution of (E)-methyl 2-(2-hydroxyphenyl)-3-methoxypropenoate (2.08g, 10 mmol) in dry THF (7 After stirring overnight, some water was added and the molecular sieves were removed by filtration. After stirring overnight again, the reaction mixture was added dropwise to another equivalent of cyanuric chloride and potassium carbonate in THF and then stirred overnight. The reaction mixture was filtered, diluted with water and then extracted thoroughly with ethyl acetate. The combined extracts were dried and evaporated to give a yellow gum (2.02g). Chromatography gave the title compound as a yellow powder (200 mg); $^1$H NMR (CDCl$_3$) $\delta$3.65(3H,s); 3.77(3H,s); 7.18-7.29(1H,m); 7.31-7.46(3H,m); 7.48(1H,s) ppm; mass spectrum m/e 355 (M+), 324, 296.

EXAMPLE 6

This Example illustrates the preparation of (E)-methyl 2-[2-(6-chloro-3-phenoxy-1,2,4-triazin-5-yloxy)-phenyl]-3-methoxypropenoate (Compound Table V).

To a stirred suspension of sodium hydride (0.99g, 1.38 mmol, 55% dispersion in oil pre-washed with dry THF) in dry THF (10 ml) under nitrogen was added phenol (2.13g, 2.76 mmol, freshly distilled). When all effervescence had ceased, the slightly cloudy solution was added dropwise to a stirred solution of 3,5,6-trichloro-1,2,4-triazine (2.10g, 11.38 mmol, prepared according to B A Loving et al., J. Het. Chem., 1971, 8, 1095-6) in dry THF (25 ml) under nitrogen. An exothermic reaction took place which gave rise to a yellow solution with a white precipitate. After 90 minutes at room temperature, the reaction mixture was filtered and evaporated to give a yellow oil (4.24g). The oil was triturated with diethyl ether-dichloromethane to afford a cream colored, sticky solid (0.79g). The trituration filtrate was evaporated to leave a pale yellow oil (3.30g). Chromatography of this oil (eluent ethyl acetate-n-hexane-acetic acid, 1:10:0.1) gave 3,5-diphenoxy-6-chloro-1,2,4-triazine as a colourless oil (1.92g) which crystallised from ether-n-hexane as a white solid (1.38g, 40.5% yield) m.p. 63°-4° C.

To a stirred solution of 3,5-diphenoxy-6-chloro-1,2,4-triazine (0.60g, 2.00 mmol) in dry THF (12 ml) at 0° C. under an atmosphere of nitrogen were added potassium carbonate (0.55g, 4.00 mmol) and some molecular sieves. To the resulting mixture was added dropwise a solution of (E)-methyl 2-(2-hydroxyphenyl)-3-methoxypropenoate (0.83 g, 4.00 mmol) in dry THF (8 ml). The temperature was allowed to reach room temperature and stirring continued overnight. The reaction mixture was cooled to 0° C. and methyl iodide (1.14g, 8.00 mmol) and potassium carbonate (0.55g, 4.00 mmol) were added. The reaction mixture was allowed slowly to warm to room temperature and then stirred over the weekend. The reaction mixture was then diluted with dichloromethane (25 ml), filtered and then washed with water (2×20 ml). The organic layer was dried and evaporated to give a light brown oil (1.73g). Repeated chromatography (eluent ethyl acetate, n-hexane, acetic acid mixtures) afforded the title compound as a thick oil (0.28g, 34%); $^1$H NMR $\delta$3.66(3H,s); 3.78(3H,s); 7.09-7.42(9H,m); 7.50(1H,s) ppm; Infrared max. 1707, 1631 cm$^{-1}$, mass spectrum m/e 413 (M+).

EXAMPLE 7

This Example illustrates the preparation of (E)-methyl 2-[2-(3-phenoxy-1,2,4-triazinyloxy)phenyl]-3-methoxypropenoate (compound No 1 of Table II).

To a stirred solution of (E)-methyl 2-[2-(6-chloro-3-phenoxy-1,2,4-triazin-5-yloxy)phenyl]-3-m (0.1 g, 0.24mmol prepared as in Example 6) in THF (4ml) containing potassium carbonate (0.116g, 0.84 mmol) and 5% palladium on carbon (20mg) was added dropwise a solution of sodium hypophosphite (0.0638g, 0.72 mmol) in water (1 ml). After stirring overnight, a second batch of each reagent was added and stirring continued overnight. A third batch of each reagent was then added and stirring continued over the weekend. Hydrogen gas was then bubbled through the reaction mixture for 5½hours. The reaction mixture was partitioned between water (5 ml) and dichloromethane (15 ml) and filtered. The dichloromethane layer was separated and the aqueous layer was extracted further with dichloromethane (2×10 ml). The combined organic extracts were dried, filtered and evaporated to give a thick, light brown oil (50mg). Chromatography on silica (eluent ether-n-hexane,3:1) afforded the title compound as a white foam (25mg, 27%); $^1$H NMR (CDCl$_3$)$\delta$3.61(3H,s); 3.72 (3H,s); 7.11-7.45 (9H,m); 7.48(1H,s) 8.71(1H,s); Infrared max. 1707, 1631cm.$^{-1}$.

EXAMPLE 8

This Example illustrates the preparation of:

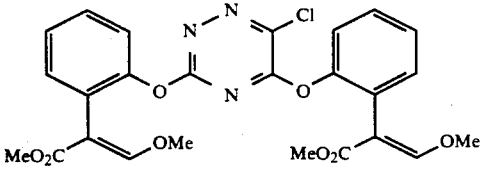

(Compound No 3 of Table V).

To a stirred solution of (E)-methyl 2-(2-hydroxyphenyl)-3-methoxypropenoate (4.16g, 20 mmol) in dry THF containing 4A molecular sieves (5 ml) and potassium carbonate (2.76g, 20 mmol) under nitrogen at 0° C. was added dropwise over 15 minutes a solution of 3,5,6-trichloro-1,2,4-triazine (3.69g, 20 mmol) in THF (25 ml). The reaction mixture was stirred at 0° C. for 30 minutes and then allowed to warm to room temperature overnight. The reaction mixture was diluted with dichloromethane, filtered and evaporated to give an orange gum (7.58g). Chromatography (eluent diethyl ether-n-hexane,1:1) gave (E)-methyl 2-[2-(3,6-dichloro-1,2,4-triazin-5-yloxy)phenyl]-3-methoxypropenoate (5,90 g, 83% colored solid; m.p. 140°-2° C., Infrared max. 1696, 1624cm$^{-1}$; $^1$H NMR (CDCl$_3$) δ3.65(3H,s); 3.78 (3H,s); 7.26-7.49(4H,m); 7.47 (1H,s) ppm.

To a stirred mixture of (E)-methyl 2-[2-(3,6-dichloro-1,2,4-triazin-5-yloxy)phenyl]-3-methoxypropenoate (0.30g, 0.84 mmol) and potassium carbonate (0.12g, 0.84 mmol) in dry acetonitrile (7 ml) at room temperature under nitrogen was added a solution of (E)-methyl 2-(2-hydroxyphenyl)-3-methoxypropenoate. Dry caesium fluoride (0.13g, 0.84 mmol) and a catalytic amount of 18-crown-6 were added and the resulting mixture stirred overnight at room temperature. The reaction mixture was filtered and evaporated to give a thick oil (0.45g). Chromatography (eluent diethyl ether-n-hexane, 2:1) afforded the title compound as a white, waxy solid (0.39g). Trituration with n-hexane gave a white powder (0.26g, 59%); m.p. 67°-70° C.; $^1$H NMR (CDCl$_3$) δ3.55(3H,s); 3 63(3H,s); 3.68(3H,s); 3.77(3H,s); 7.10-7.41(8H,m); 7.42(1H,s); 7.52(1H,s) ppm; mass spectrum m/e 527 (M+).

EXAMPLE 9

This Example illustrates the preparation of:

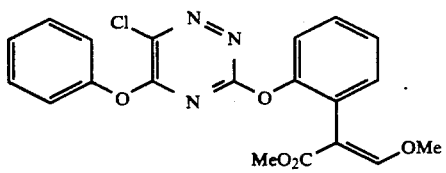

(Compound No. 1 of Table VI).

To the product of Example 8 (0.15g, 0.284 mmol) in dry THF (3 ml) at 0° C. under nitrogen, were added potassium carbonate (0.039g, 0.284 mmol) and some 4Å molecular sieves. A solution containing freshly distilled phenol (0.027 mg, 0.284 mmol) in dry THF (1 ml) was added dropwise with stirring and the reaction mixture stirred overnight at room temperature. More phenol (0.027 mg, 0.284 mmol) and potassium carbonate (0.039g, 0.284 mmol) were added and stirring continued over the weekend. The reaction mixture was poured into water (8 ml) and then extracted with dichloromethane (3×15 ml). extracts were dried and evaporated to give a brown oil (0.18g). Chromatography (eluent diethyl ether-n-hexane, 3:2) gave an oil (67 mg) which was re-chromatographed (eluent ethyl acetate-n-hexane-acetic acid, 2:7:0.1) to afford (after washing with base to remove traces of acetic acid) the title compound as a waxy gum (37 mg); $^1$H NMR (CDCl$_3$) δ3.55(3H,s); 3.70(3H,s); 7.10-7.48(9H,m); 7.41(1H,s) ppm; Infrared max. 1708, 1631 cm$^{-1}$; mass spectrum m/e 413 (M+). A repeat preparation on a larger scale (1.71 mmol) yielded the product as a yellow foam (0.44g).

EXAMPLE 10

This Example illustrates the preparation of (E)-methyl 2-[2-(5-phenoxy-1,2,4-triazin-3-yloxy)phenyl]-3-methoxypropenoate (Compound No. 115).

To the product of Example 9 (0.30g, 0.725 mmol) in THF (20 ml) were added potassium carbonate (0.35g, 2.54 mmol), 5% palladium on carbon (45 mg) and then water (1.5 ml). Hydrogen gas was then bubbled through the stirred mixture at room temperature. After 3½hours, the mixture was diluted with water (15 ml) and dichloromethane (20 ml) and filtered. The dichloromethane layer was separated and the aqueous layer was extracted further with dichloromethane (2×20 ml). The combined organic extracts were dried, filtered and evaporated to give a pale yellow oil (0.44g). Chromatography (eluent diethyl ether-n-hexane, 3:1) gave a waxy white foam (0.18g) which crystallised from cold diethyl ether-n-hexane (containing a trace of dichloromethane) to afford the title compound as a white powder (0.17g, 63%); m.p. 78°-80° C.; Infrared max. 1708, 1631 cm$^{-1}$; $^1$H NMR (CDCl$_3$) δ3.56(3H,s); 3.70(3H,s); 7.13-7.47(9H,m); 7.41(1H,s); 8.79(1H,s) ppm; mass spectrum m/e 379 (M+).

The following are examples of compositions suitable for agricultural and horticultural purposes which can be formulated from the compounds of the invention. Such compositions form another aspect of the invention. Percentages are by weight.

EXAMPLE 11

An emulsifiable concentrate is made up by mixing and stirring the ingredients until all are dissolved.

| | |
|---|---|
| Compound No. 7 of Table I | 10% |
| Benzyl alcohol | 30% |
| Calcium dodecylbenzenesulphonate | 5% |
| Nonylphenolethoxylate (13 mole ethylene oxide) | 10% |
| Alkyl benzenes | 45% |

EXAMPLE 12

The active ingredient is dissolved in methylene dichloride and the resultant liquid sprayed on to the granules of attapulgite clay. The solvent is then allowed to evaporate to produce a granular composition.

| | |
|---|---|
| Compound No. 7 of Table I | 5% |
| Attapulgite granules | 95% |

EXAMPLE 13

A composition suitable for use as a seed dressing is prepared by grinding and mixing the three ingredients.

| | |
|---|---|
| Compound No. 7 of Table I | 50% |
| Mineral oil | 2% |
| China clay | 48% |

EXAMPLE 14

A dustable powder is prepared by grinding and mixing the active ingredient with talc.

| | |
|---|---|
| Compound No. 7 of Table I | 5% |
| Talc | 95% |

EXAMPLE 15

A suspension concentrate is prepared by ball milling the ingredients to form an aqueous suspension of the ground mixture with water.

| | |
|---|---|
| Compound No. 7 of Table I | 40% |
| Sodium lignosulphonate | 10% |
| Bentonite clay | 1% |
| Water | 49% |

This formulation can be used as a spray by diluting into water or applied directly to seed.

EXAMPLE 16

A wettable powder formulation is made by mixing together and grinding the ingredients until all are thoroughly mixed.

| | |
|---|---|
| Compound No. 7 of Table I | 25% |
| Sodium lauryl sulphate | 2% |
| Sodium lignosulphonate | 5% |
| Silica | 25% |
| China clay | 43% |

EXAMPLE 17

The compounds were tested against a variety of foliar fungal diseases of plants. The technique employed was as follows.

The plants were grown in John Innes Potting Compost (no 1 or 2) in 4cm diameter minipots. The test compounds were formulated either by bead milling with aqueous Dispersol T or as a solution in acetone or acetone/ethanol which was diluted to the required concentration immediately before use. For the foliage diseases, the formulations (100 ppm active ingredient) were sprayed onto the foliage and applied to the roots of the plants in the soil. Alternatively, the compounds were applied as a foliar spray only at a concentration of 10 ppm or 25 ppm. The sprays were applied to maximum retention and the root drenches to a final concentration equivalent to approximately 40 ppm a.i. in dry soil. Tween 20, to give a final concentration of 0.05%, was added when the sprays were applied to cereals.

For most of the tests the compound was applied to the soil (roots) and to the foliage (by spraying) one or two days before the plant was inoculated with the disease. An exception was the test on *Erysiphe graminis* in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:

| | |
|---|---|
| 4 = | no disease |
| 3 = | trace-5% of disease on untreated plants |
| 2 = | 6-25% of disease on untreated plants |
| 1 = | 26-59% of disease on untreated plants |
| 0 = | 60-100% of disease on untreated plants |

The results are shown in Table VIII.

In Table VIII the following abbreviations are used:

| | |
|---|---|
| Pr = | *Puccinia recondita* (wheat) |
| Egh = | *Erysiphe graminis hordei* (barley) |
| Egt = | *Erysiphe graminis tritici* (wheat) |
| Sn = | *Septoria nodorum* (wheat) |
| Vi = | *Venturia inaequalis* (apple) |
| Po = | *Pyricularia oryzae* (rice) |
| Tc = | *Thanatephorus cucumeris* (rice) |
| Ca = | *Cercospora arachidicola* (peanut) |
| Pv = | *Plasmopara viticola* (vine) |
| Pil = | *Phytophthora infestans lycopersici* (tomato) |

TABLE VIII

| COMPOUND No | TABLE No | Pr | Egh | Egt | Sn | Vi | Po | Tc | Ca | Pv | Pil |
|---|---|---|---|---|---|---|---|---|---|---|---|
| 1 | I | 4a | 4a | — | — | 4a | 3a | — | 4a | 4a | 4a |
| 7 | I | 4 | 4 | — | — | 4 | 4 | — | 4 | 4 | — |
| 11 | I | 4 | 4 | — | — | 4 | 4 | — | 4 | 4 | 4 |
| 13 | I | 4 | — | — | — | 4 | 3 | — | 4 | 4 | 4 |
| 15 | I | 4 | 2 | — | — | 4 | 4 | — | 2 | 4 | 4 |
| 243 | I | 4 | — | 4 | 2 | 4 | — | — | — | 4 | — |
| 1 | II | 0a | 0a | — | 0a | 0b | 0a | 0b | — | 3a | 0b |
| 229 | II | 0 | 0 | — | 3 | 4 | 0 | 1 | — | 4 | 2 |
| 1 | III | — | 4 | — | — | 4 | 3 | — | 4 | 4 | 4 |
| 115 | III | 4a | 3a | — | — | 4a | 2a | — | 4a | 4a | 2a |
| 116 | III | 4 | 4 | — | — | 4 | — | — | — | 4 | 4 |
| 119 | III | 4 | — | 4 | 4 | 4 | 4 | — | — | 4 | — |
| 122 | III | 4a | — | 0a | 3a | 4a | 4a | — | — | 4a | — |
| 123 | III | 3a | 0a | — | — | 3a | 1a | — | 3a | 4a | 0a |
| 143 | III | 4 | 4 | — | — | 4 | 4 | — | — | 4 | 4 |
| 175 | III | 4 | 4 | — | — | 4 | 4 | — | — | 4 | 4 |
| 178 | III | 4 | 4 | — | 3 | 4 | 4 | 4 | — | 4 | 3 |

TABLE VIII-continued

| COMPOUND No | TABLE No | Pr | Egh | Egt | Sn | Vi | Po | Tc | Ca | Pv | Pil |
|---|---|---|---|---|---|---|---|---|---|---|---|
| 229 | III | 4 | 4 | — | — | 4 | 4 | 4 | — | 4 | 4 |
| 230 | III | 4 | — | 4 | 4 | 4 | 4 | 4 | — | 4 | 4 |
| 231 | III | 4 | — | 4 | 2 | 4 | 4 | — | — | 4 | — |
| 1 | IV | 3 | 0 | — | — | 4 | — | — | 3 | 4 | 0 |
| 2 | IV | 3 | 0 | — | — | 3 | 0 | — | 3 | 4 | 4 |
| 3 | IV | 3 | 0 | — | — | 4 | 3 | — | — | 4 | 1 |
| 4 | IV | 4 | 0 | — | — | 4 | 2 | — | — | 4 | 4 |
| 5 | IV | 2 | 1 | — | — | 4 | 4 | 0 | — | 4 | 4 |
| 6 | IV | 4 | 0 | — | — | 3 | — | — | — | 4 | 0 |
| 7 | IV | 4 | 0 | — | — | 4 | — | — | — | 3 | 0 |
| 8 | IV | 4 | 0 | — | 3 | 4 | 3 | 1 | — | 4 | 0 |
| 9 | IV | 0 | 0 | — | 3 | 0 | 2 | 0 | — | 4 | 3 |
| 10 | IV | 3 | 0 | — | 4 | 4 | 0 | 1 | — | 4 | 3 |
| 2 | V | 0 | 0 | — | 3 | 0 | 0 | 0 | — | 4 | 1 |
| 3 | V | 0a | — | 0a | 0a | 1a | 0a | 0a | — | 0a | 0a | a 10 ppm foliar spray only
b 25 ppm foliar spray only
— no result

We claim:
1. A compound having the formula (I):

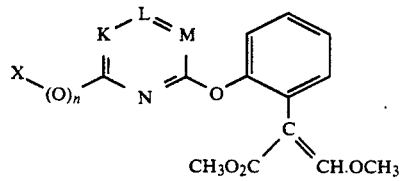

in which K and M are nitrogen and L is CY wherein Y is H, halogen $C_{1-4}$ alkyl, $C_{1-4}$ alkoxy, cyano, nitro or trifluoromethyl; n is 0 or 1; and X is optionally substituted phenyl or an optionally substituted heteroaromatic ring selected from the group consisting of thiophene, pyrrole, imidazole, pyrazole, thiazole, isothiazole, oxazole, isoxazole, 1,2,4-triazole, 1,2,3-triazole, 1,2,4-thiadiazole, 1,3,4-thiadiazole, pyridine, pyrimidine, pyrazine, pyridazine, 1,2,4-triazine and 1,3,5-triazine, the optional substituents of the optionally substituted phenyl or heteroaromatic ring X being selected from one or more of the group consisting of halogen; $C_{1-4}$ alkyl, $C_{3-6}$ cycloalkyl, $C_{2-4}$ alkenyl, $C_{2-4}$ alkynyl, $C_{2-4}$ alkenyloxy, thiocyanato, isothiocyanato, nitro, $NR^1R^2$, $NR^1OR^2$, $N_3$, $NHCOR^1$, $NR^1COR^2$, $NHCONR^1R^2$, $N=CHNR^1R^2$, $NHSO_2R^1$, $OR^1$, $OCOR^1$, $OSO_2R^2$, $SR^1$, $SOR^1$, $SO_2R^1$, $SO_2OR^1$, $SO_2NR^1R^2$, $COR^1$, $CR^1=NOR^2$, $CHR^1CO_2R^2$, $CO_2R^1$, $CONR^1R^2$, $CSNR^1R^2$, $CH_3O_2C.C$; $CH.OCH_3$, 1-(imidazol-1-yl)vinyl, furyl, thienyl, pyrrolyl, imidazolyl, pyrazolyl, thiazolyl, isothiazolyl, oxazolyl, isoxazolyl, 1,2,4-triazolyl, 1,2,3-triazolyl, 1,2,4-thiadiazolyl, 1,3,4-thiadiazolyl, pyridinyl, pyrimidinyl, pyrazinyl, pyridazinyl, 1,2,4-triazinyl or 1,3,5-triazinyl or, when X is phenyl, two substituents ortho to one another, join to form a fused benzene, pyridine, thiophene or imidazole ring or a methylenedioxy group; $R^1$ and $R^2$ being independently hydrogen, $C_{1-4}$ alkyl, $C_{2-4}$ alkenyl or phenyl, and any of the foregoing aliphatic moieties being optionally substituted with one or more of halogen, cyano, $OR^1$, $SR^1$, $NR^1R^2$, $SiR^1_3$ or $OCOR^1$ and any of the foregoing phenyl moieties being optionally substituted with one or more of halogen, $C_{1-4}$ alkyl, $C_{1-4}$ alkoxy, nitro or cyano.

2. A compound according to claim 1 in which the optional substituents of the optionally substituted phenyl or heteroaromatic ring X are selected from one or more of the group consisting of halogen, $C_{1-4}$ alkyl, $C_{3-6}$ cycloalkyl, $C_{2-4}$ alkenyl, $C_{2-4}$ alkynyl, $C_{2-4}$ alkenyloxy, $C_{2-4}$ alkynyloxy, phenyl, benzyloxy, cyano, isocyano, thiocyanato, isothiocyanato, nitro, $NR^1R^2$, $NHCOR^1$, $NMCONR^1R^2$, $NHSO_2R^1$, $OR_1$, $OCOR^1$, $OSO_2R^1$, $SR^1$, $SOR^1$, $SO_2R^1$, $COR^1$, $CR-=NOR^2$, $CO_2R^1$, $CONR^1R^2$, $CSNR^1R^2$; or, when X is phenyl, two substituents ortho to one another, join to form a fused benzene, pyridine, thiophene or imidazole ring or a methylenedioxy group; $R^1$ and $R^2$ being independently hydrogen, $C_{1-4}$ alkyl or phenyl, aliphatic moieties of any of the substituents being themselves optionally substituted with one or more of halogen, cyano, $OR^1$ or $OCOR^1$ and the phenyl moieties of any of the substituents being themselves optionally substituted with one ore more of halogen, $C_{1-4}$ alkyl, $C_{1-4}$ alkoxy, nitro or cyano.

3. Compounds according to claim 1 in which Y is H or halogen.

4. A fungicidal composition comprising a fungicidally effective amount of a compound according to claim 1 and a fungicidally acceptable carrier or diluent therefor.

5. A method of combating fungi which comprises applying to plants, to the seeds of plants or to the locus of the plants or seeds a fungicidally effective amount of compound according to claim 1.

6. A compound of formula (I.2):

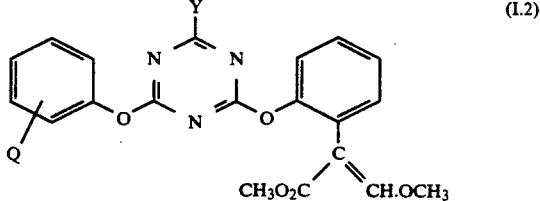

in which Y is H or chlorine and Q is halogen, $C_{1-4}$ alkyl, $C_{1-4}$ alkoxy, cyano, nitro trifluoromethyl or $CH_3O_2C.C:CH.OCH_3$.

* * * * *